US012761152B2

(12) United States Patent
Ammar et al.

(10) Patent No.: US 12,761,152 B2
(45) Date of Patent: Oct. 13, 2026

(54) MULTI-SPECTROSCOPY ROCK CHARACTERIZATION SYSTEM

(71) Applicant: Schlumberger Technology Corporation, Sugar Land, TX (US)

(72) Inventors: Mahdi Ammar, Dhahran (SA); Ngoc Hoang Lan Huynh, Clamart (FR); Simone Di Santo, Dhahran (SA); Karim Bondabou, Clamart (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 68 days.

(21) Appl. No.: 19/073,660

(22) Filed: Mar. 7, 2025

(65) Prior Publication Data

US 2025/0283823 A1 Sep. 11, 2025

Related U.S. Application Data

(60) Provisional application No. 63/562,864, filed on Mar. 8, 2024.

(51) Int. Cl.

| | |
|---|---|
| ***G01N 21/64*** | (2006.01) |
| ***G01N 33/24*** | (2006.01) |
| ***G06V 10/143*** | (2022.01) |
| ***G06V 10/145*** | (2022.01) |
| ***G06V 10/147*** | (2022.01) |
| ***G06V 20/69*** | (2022.01) |

(52) U.S. Cl.

CPC ....... *G01N 21/6458* (2013.01); *G01N 33/241* (2013.01); *G06V 10/143* (2022.01); *G06V 10/145* (2022.01); *G06V 10/147* (2022.01); *G06V 20/693* (2022.01)

(58) Field of Classification Search

CPC ............ G01N 21/6458; G01N 33/241; G01N 21/6456; G01N 21/01; G01N 21/84; G06V 10/143; G06V 10/145; G06V 10/147; G06V 20/693; E21B 49/005

See application file for complete search history.

(56) References Cited

U.S. PATENT DOCUMENTS

2017/0298726 A1* 10/2017 Smith .................. E21B 49/005
2026/0146531 A1 5/2026 Di Santo et al.

FOREIGN PATENT DOCUMENTS

RU 2323457 C2 * 4/2008 ................ G01J 3/06

OTHER PUBLICATIONS

Ablard, P., et al., "The expanding role of mud logging", Oilfield Review, 2012, pp. 24-41, vol. 24, No. 1.

Delaune, P. L., et al., "Enhanced Wellsite Technique for Oil Detection and Characterization", SPE 56802, SPE Annual Technical Conference and Exhibition, Oct. 3, 1999, pp. 1-16.

(Continued)

*Primary Examiner* — Kiho Kim
(74) *Attorney, Agent, or Firm* — Jeffrey D. Frantz

(57) ABSTRACT

A system can include a white light source; an ultraviolet light source; a digital machine vision camera for capture of imagery of rock cutting samples illuminated by the white light source and the ultraviolet light source; and circuitry operable to generate calibrated imagery of rock cuttings samples with contrast between rock cuttings samples with hydrocarbons and rock cuttings samples without hydrocarbons.

20 Claims, 14 Drawing Sheets

(56) References Cited

OTHER PUBLICATIONS

Liu, K., et al., "Advances in Fluorescence Spectroscopy for Petroleum Geosciences", Chapter 4, Royal Society of Chemistry, pp. 94-121.
Reyes, M. V., "Application of fluorescence techniques for mudlogging analysis of oil drilled with oil-based muds," SPE Formation Evaluation, Dec. 1994, pp. 300-305, vol. 9, No. 4.
Riecker, R. E., "Hydrocarbon Fluorescence and Migration of Petroleum", AAPG Bulletin, Jan. 1962, pp. 60-75, vol. 46, No. 1.
Santo, S., D., "The digital revolution in mudlogging: An inno-vative workflow for advanced analysis and classification of drill cuttings using computer vision and machine-learning," Second International Meeting for Applied Geoscience & Energy, 2022, pp. 1875-1879.

* cited by examiner

400

600

610

910

920

White 1110

UV 1120

MULTI-SPECTROSCOPY ROCK CHARACTERIZATION SYSTEM

RELATED APPLICATION

This application claims priority to and the benefit of a U.S. Provisional application having Ser. No. 63/562,864, filed 8 Mar. 2024, which is incorporated by reference herein in its entirety.

BACKGROUND

A resource field may be an accumulation, pool or group of pools of one or more resources (e.g., oil, gas, oil and gas) in a subsurface environment. A resource field may include at least one reservoir. A reservoir may be shaped in a manner that may trap hydrocarbons and may be covered by an impermeable or sealing rock. A bore may be drilled into an environment where the bore may be utilized to form a well that may be utilized in producing hydrocarbons from a reservoir.

A rig may be a system of components that may be operated to form a bore in an environment, to transport equipment into and out of a bore in an environment, etc. As an example, a rig may include a system that may be used to drill a bore and to acquire information about an environment, about drilling, etc. A resource field may be an onshore field, an offshore field or an on- and offshore field. A rig may include components for performing operations onshore and/or offshore. A rig may be, for example, vessel-based, offshore platform-based, onshore, etc.

Field planning may occur over one or more phases, which may include an exploration phase that aims to identify and assess an environment (e.g., a prospect, a play, etc.), which may include drilling of one or more bores (e.g., one or more exploratory wells, etc.). Other phases may include appraisal, development and production phases.

In various instances, material from drilling may be assessed, for example, to characterize a formation, etc. For example, consider assessment of cuttings as may be pieces of broken rock of a formation that may be transported from downhole to surface via circulation of drilling fluid. Such an assessment may depend on human observations of the cuttings, which may be subjective and inconsistent. Where characterizations based on cuttings can be improved, drilling may be improved.

SUMMARY

A system can include a white light source; an ultraviolet light source; a digital machine vision camera for capture of imagery of rock cutting samples illuminated by the white light source and the ultraviolet light source; and circuitry operable to generate calibrated imagery of rock cuttings samples with contrast between rock cuttings samples with hydrocarbons and rock cuttings samples without hydrocarbons. A method can include illuminating a rock cuttings sample with white light and ultraviolet light; capturing imagery of the rock cuttings sample; and characterizing the rock cuttings sample based at least in part on physical characteristics derived from the imagery and based at least in part on fluorescent emissions derived from the imagery. One or more computer-readable storage media can include computer-executable instructions executable to instruct a computing system to: illuminate a rock cuttings sample with white light and ultraviolet light; capture imagery of the rock cuttings sample; and characterize the rock cuttings sample based at least in part on physical characteristics derived from the imagery and based at least in part on fluorescent emissions derived from the imagery. Various other apparatuses, systems, methods, etc., are also disclosed.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Features and advantages of the described implementations may be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Figure 1:
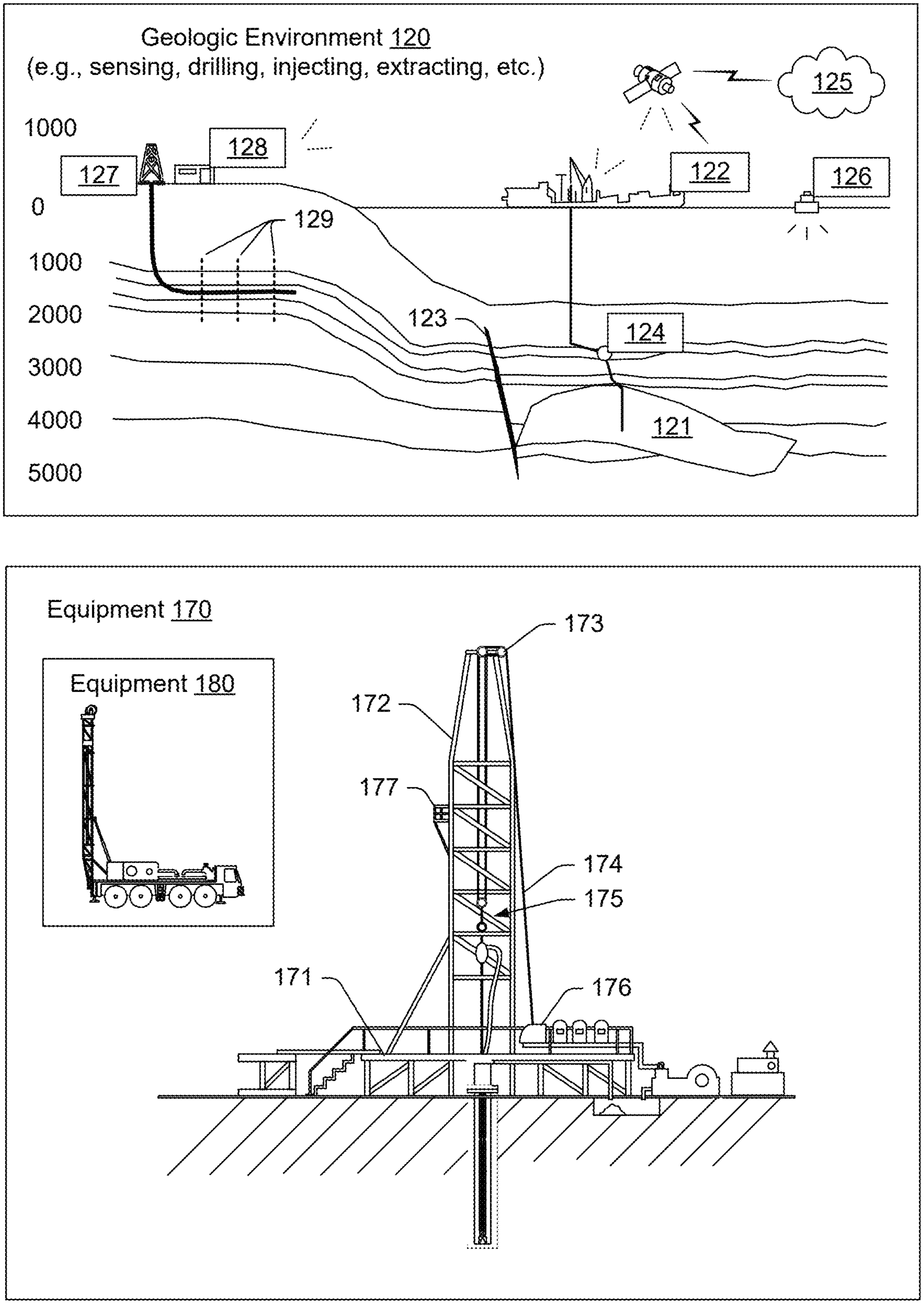
FIG. 1 illustrates examples of equipment in a geologic environment.

FIG. 1 shows an example of a geologic environment 120. In FIG. 1, the geologic environment 120 may be a sedimentary basin that includes layers (e.g., stratification) that include a reservoir 121 and that may be, for example, intersected by a fault 123 (e.g., or faults). As an example, the geologic environment 120 may be outfitted with a variety of sensors, detectors, actuators, etc. For example, equipment 122 may include communication circuitry to receive and to transmit information with respect to one or more networks 125. Such information may include information associated with downhole equipment 124, which may be equipment to acquire information, to assist with resource recovery, etc. Other equipment 126 may be located remote from a well site and include sensing, detecting, emitting or other circuitry. Such equipment may include storage and communication circuitry to store and to communicate data, instructions, etc. As an example, one or more pieces of equipment may provide for measurement, collection, communication, storage, analysis, etc. of data (e.g., for one or more produced resources, etc.). As an example, one or more satellites may be provided for purposes of communications, data acquisition, etc. For example, FIG. 1 shows a satellite in communication with the network 125 that may be configured for communications, noting that the satellite may additionally or alternatively include circuitry for imagery (e.g., spatial, spectral, temporal, radiometric, etc.).

FIG. 1 also shows the geologic environment 120 as optionally including equipment 127 and 128 associated with a well that includes a substantially horizontal portion that may intersect with one or more fractures 129. For example, consider a well in a shale formation that may include natural fractures, artificial fractures (e.g., hydraulic fractures) or a combination of natural and artificial fractures. As an example, a well may be drilled for a reservoir that is laterally extensive. In such an example, lateral variations in properties, stresses, etc. may exist where an assessment of such variations may assist with planning, operations, etc. to develop the reservoir (e.g., via fracturing, injecting, extracting, etc.). As an example, the equipment 127 and/or 128 may include components, a system, systems, etc. for fracturing, seismic sensing, analysis of seismic data, assessment of one or more fractures, injection, production, etc. As an example, the equipment 127 and/or 128 may provide for measurement, collection, communication, storage, analysis, etc. of data such as, for example, production data (e.g., for one or more produced resources). As an example, one or more satellites may be provided for purposes of communications, data acquisition, etc.

FIG. 1 also shows an example of equipment 170 and an example of equipment 180. Such equipment, which may be systems of components, may be suitable for use in the geologic environment 120. While the equipment 170 and 180 are illustrated as land-based, various components may be suitable for use in an offshore system.

The equipment 170 includes a platform 171, a derrick 172, a crown block 173, a line 174, a traveling block assembly 175, drawworks 176 and a landing 177 (e.g., a monkeyboard). As an example, the line 174 may be controlled at least in part via the drawworks 176 such that the traveling block assembly 175 travels in a vertical direction with respect to the platform 171. For example, by drawing the line 174 in, the drawworks 176 may cause the line 174 to run through the crown block 173 and lift the traveling block assembly 175 skyward away from the platform 171; whereas, by allowing the line 174 out, the drawworks 176 may cause the line 174 to run through the crown block 173 and lower the traveling block assembly 175 toward the platform 171. Where the traveling block assembly 175 carries pipe (e.g., casing, etc.), tracking of movement of the traveling block 175 may provide an indication as to how much pipe has been deployed.

A derrick may be a structure used to support a crown block and a traveling block operatively coupled to the crown block at least in part via line. A derrick may be pyramidal in shape and offer a suitable strength-to-weight ratio. A derrick may be movable as a unit or in a piece-by-piece manner (e.g., to be assembled and disassembled).

As an example, drawworks may include a spool, brakes, a power source and assorted auxiliary devices. Drawworks may controllably reel out and reel in line. Line may be reeled over a crown block and coupled to a traveling block to gain mechanical advantage in a "block and tackle" or "pulley" fashion. Reeling out and in of line may cause a traveling block (e.g., and whatever may be hanging underneath it), to be lowered into or raised out of a bore. Reeling out of line may be powered by gravity and reeling in by a motor, an engine, etc. (e.g., an electric motor, a diesel engine, etc.).

As an example, a crown block may include a set of pulleys (e.g., sheaves) that may be located at or near a top of a derrick or a mast, over which line is threaded. A traveling block may include a set of sheaves that may be moved up and down in a derrick or a mast via line threaded in the set of sheaves of the traveling block and in the set of sheaves of a crown block. A crown block, a traveling block and a line may form a pulley system of a derrick or a mast, which may enable handling of heavy loads (e.g., drillstring, pipe, casing, liners, etc.) to be lifted out of or lowered into a bore. As an example, line may be about a centimeter to about five centimeters in diameter as, for example, steel cable. Through use of a set of sheaves, such line may carry loads heavier than the line could support as a single strand.

As an example, a derrickman may be a rig crew member that works on a platform attached to a derrick or a mast. A derrick may include a landing on which a derrickman may stand. As an example, such a landing may be about 10 meters or more above a rig floor. In an operation referred to as trip out of the hole (TOH), a derrickman may wear a safety harness that enables leaning out from the work landing (e.g., monkeyboard) to reach pipe in located at or near the center of a derrick or a mast and to throw a line around the pipe and pull it back into its storage location (e.g., fingerboards), for example, until it a time at which it may be desirable to run the pipe back into the bore. As an example, a rig may include automated pipe-handling equipment such that the derrickman controls the machinery rather than physically handling the pipe.

As an example, a trip may refer to the act of pulling equipment from a bore and/or placing equipment in a bore. As an example, equipment may include a drillstring that may be pulled out of a hole and/or placed or replaced in a hole. As an example, a pipe trip may be performed where a drill bit has dulled or has otherwise ceased to drill efficiently and is to be replaced.

Figure 2:
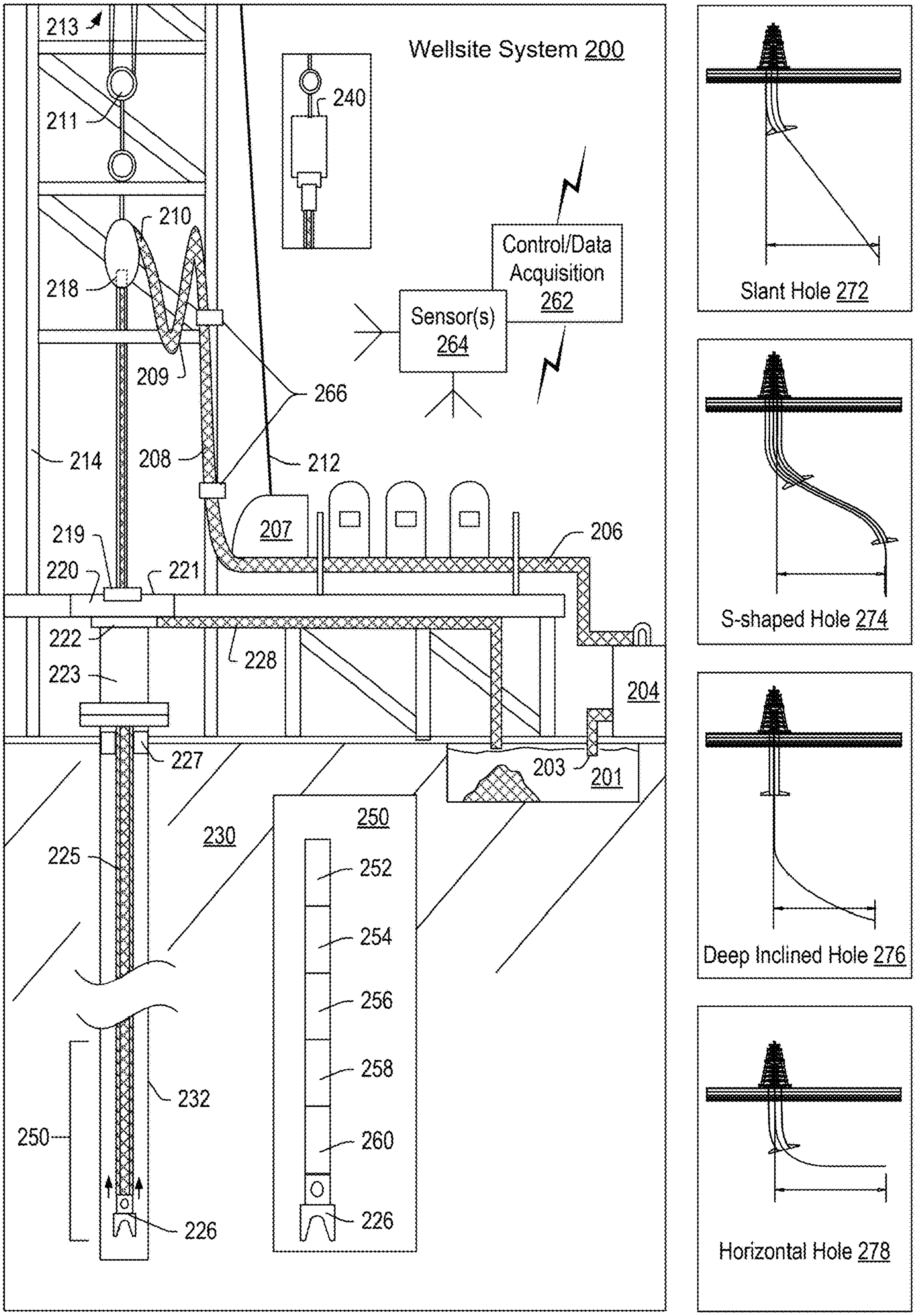
FIG. 2 illustrates examples of equipment and examples of hole types.

FIG. 2 shows an example of a wellsite system 200 (e.g., at a wellsite that may be onshore or offshore). As shown, the wellsite system 200 may include a mud tank 201 for holding mud and other material (e.g., where mud may be a drilling fluid), a suction line 203 that serves as an inlet to a mud pump 204 for pumping mud from the mud tank 201 such that mud flows to a vibrating hose 206, a drawworks 207 for winching drill line or drill lines 212, a standpipe 208 that receives mud from the vibrating hose 206, a kelly hose 209 that receives mud from the standpipe 208, a gooseneck or goosenecks 210, a traveling block 211, a crown block 213 for carrying the traveling block 211 via the drill line or drill lines 212 (see, e.g., the crown block 173 of FIG. 1), a derrick 214 (see, e.g., the derrick 172 of FIG. 1), a kelly 218 or a top drive 240, a kelly drive bushing 219, a rotary table 220, a drill floor 221, a bell nipple 222, one or more blowout preventors (BOPs) 223, a drillstring 225, a drill bit 226, a casing head 227 and a flow pipe 228 that carries mud and other material to, for example, the mud tank 201.

In the example system of FIG. 2, a borehole 232 is formed in subsurface formations 230 by rotary drilling; noting that various example embodiments may also use directional drilling.

As shown in the example of FIG. 2, the drillstring 225 is suspended within the borehole 232 and has a drillstring assembly 250 that includes the drill bit 226 at its lower end. As an example, the drillstring assembly 250 may be a bottom hole assembly (BHA).

The wellsite system 200 may provide for operation of the drillstring 225 and other operations. As shown, the wellsite system 200 includes the platform 211 and the derrick 214 positioned over the borehole 232. As mentioned, the wellsite system 200 may include the rotary table 220 where the drillstring 225 pass through an opening in the rotary table 220.

As shown in the example of FIG. 2, the wellsite system 200 may include the kelly 218 and associated components, etc., or a top drive 240 and associated components. As to a kelly example, the kelly 218 may be a square or hexagonal metal/alloy bar with a hole drilled therein that serves as a mud flow path. The kelly 218 may be used to transmit rotary motion from the rotary table 220 via the kelly drive bushing 219 to the drillstring 225, while allowing the drillstring 225 to be lowered or raised during rotation. The kelly 218 may pass through the kelly drive bushing 219, which may be driven by the rotary table 220. As an example, the rotary table 220 may include a master bushing that operatively couples to the kelly drive bushing 219 such that rotation of the rotary table 220 may turn the kelly drive bushing 219 and hence the kelly 218. The kelly drive bushing 219 may include an inside profile matching an outside profile (e.g., square, hexagonal, etc.) of the kelly 218; however, with slightly larger dimensions so that the kelly 218 may freely move up and down inside the kelly drive bushing 219.

As to a top drive example, the top drive 240 may provide functions performed by a kelly and a rotary table. The top drive 240 may turn the drillstring 225. As an example, the top drive 240 may include one or more motors (e.g., electric and/or hydraulic) connected with appropriate gearing to a short section of pipe called a quill, that in turn may be screwed into a saver sub or the drillstring 225 itself. The top drive 240 may be suspended from the traveling block 211, so the rotary mechanism is free to travel up and down the derrick 214. As an example, a top drive 240 may allow for drilling to be performed with more joint stands than a kelly/rotary table approach.

In the example of FIG. 2, the mud tank 201 may hold mud, which may be one or more types of drilling fluids. As an example, a wellbore may be drilled to produce fluid, inject fluid or both (e.g., hydrocarbons, minerals, water, etc.).

In the example of FIG. 2, the drillstring 225 (e.g., including one or more downhole tools) may be composed of a series of pipes threadably connected together to form a long tube with the drill bit 226 at the lower end thereof. As the drillstring 225 is advanced into a wellbore for drilling, at some point in time prior to or coincident with drilling, the mud may be pumped by the pump 204 from the mud tank 201 (e.g., or other source) via the lines 206, 208 and 209 to a port of the kelly 218 or, for example, to a port of the top drive 240. The mud may then flow via a passage (e.g., or passages) in the drillstring 225 and out of ports located on the drill bit 226 (see, e.g., a directional arrow). As the mud exits the drillstring 225 via ports in the drill bit 226, it may then circulate upwardly through an annular region between an outer surface(s) of the drillstring 225 and surrounding wall(s) (e.g., open borehole, casing, etc.), as indicated by directional arrows. In such a manner, the mud lubricates the drill bit 226 and carries heat energy (e.g., frictional or other energy) and formation cuttings to the surface where the mud (e.g., and cuttings) may be returned to the mud tank 201, for example, for recirculation (e.g., with processing to remove cuttings, etc.).

The mud pumped by the pump 204 into the drillstring 225 may, after exiting the drillstring 225, form a mudcake that lines the wellbore which, among other functions, may reduce friction between the drillstring 225 and surrounding wall(s) (e.g., borehole, casing, etc.). A reduction in friction may facilitate advancing or retracting the drillstring 225. During a drilling operation, the entire drillstring 225 may be pulled from a wellbore and optionally replaced, for example, with a new or sharpened drill bit, a smaller diameter drillstring, etc. As mentioned, the act of pulling a drillstring out of a hole or replacing it in a hole is referred to as tripping. A trip may be referred to as an upward trip or an outward trip or as a downward trip or an inward trip depending on trip direction.

As an example, consider a downward trip where upon arrival of the drill bit 226 of the drillstring 225 at a bottom of a wellbore, pumping of the mud commences to lubricate the drill bit 226 for purposes of drilling to enlarge the wellbore. As mentioned, the mud may be pumped by the pump 204 into a passage of the drillstring 225 and, upon filling of the passage, the mud may be used as a transmission medium to transmit energy, for example, energy that may encode information as in mud-pulse telemetry.

As an example, mud-pulse telemetry equipment may include a downhole device configured to effect changes in pressure in the mud to create an acoustic wave or waves upon which information may modulated. In such an example, information from downhole equipment (e.g., one or more modules of the drillstring 225) may be transmitted uphole to an uphole device, which may relay such information to other equipment for processing, control, etc.

As an example, telemetry equipment may operate via transmission of energy via the drillstring 225 itself. For example, consider a signal generator that imparts coded energy signals to the drillstring 225 and repeaters that may receive such energy and repeat it to further transmit the coded energy signals (e.g., information, etc.).

As an example, the drillstring 225 may be fitted with telemetry equipment 252 that includes a rotatable drive shaft, a turbine impeller mechanically coupled to the drive shaft such that the mud may cause the turbine impeller to rotate, a modulator rotor mechanically coupled to the drive shaft such that rotation of the turbine impeller causes said modulator rotor to rotate, a modulator stator mounted adjacent to or proximate to the modulator rotor such that rotation of the modulator rotor relative to the modulator stator creates pressure pulses in the mud, and a controllable brake for selectively braking rotation of the modulator rotor to modulate pressure pulses. In such example, an alternator may be coupled to the aforementioned drive shaft where the alternator includes at least one stator winding electrically coupled to a control circuit to selectively short the at least one stator winding to electromagnetically brake the alternator and thereby selectively brake rotation of the modulator rotor to modulate the pressure pulses in the mud.

In the example of FIG. 2, an uphole control and/or data acquisition system 262 may include circuitry to sense pressure pulses generated by telemetry equipment 252 and, for example, communicate sensed pressure pulses or information derived therefrom for process, control, etc.

The assembly 250 of the illustrated example includes a logging-while-drilling (LWD) module 254 (e.g., a LWD tool), a measuring-while-drilling (MWD) module 256 (e.g., a MWD tool), an optional module 258, a roto-steerable system (RSS) and/or motor 260, and the drill bit 226. Such components or modules may be referred to as tools where a drillstring may include a plurality of tools.

As to an RSS, it involves technology utilized for directional drilling. Directional drilling involves drilling into the Earth to form a deviated bore such that the trajectory of the bore is not vertical; rather, the trajectory deviates from vertical along one or more portions of the bore. As an example, consider a target that is located at a lateral distance from a surface location where a rig may be stationed. In such an example, drilling may commence with a vertical portion and then deviate from vertical such that the bore is aimed at the target and, eventually, reaches the target. Directional drilling may be implemented where a target may be inaccessible from a vertical location at the surface of the Earth, where material exists in the Earth that may impede drilling or otherwise be detrimental (e.g., consider a salt dome, etc.), where a formation is laterally extensive (e.g., consider a relatively thin yet laterally extensive reservoir), where multiple bores are to be drilled from a single surface bore, where a relief well is desired, etc.

One approach to directional drilling involves a mud motor; however, a mud motor may present some challenges depending on factors such as rate of penetration (ROP), transferring weight to a bit (e.g., weight on bit, WOB) due to friction, etc. A mud motor may be a positive displacement motor (PDM) that operates to drive a bit (e.g., during directional drilling, etc.). A PDM operates as drilling fluid is pumped through it where the PDM converts hydraulic power of the drilling fluid into mechanical power to cause the bit to rotate.

As an example, a PDM may operate in a combined rotating mode where surface equipment is utilized to rotate a bit of a drillstring (e.g., a rotary table, a top drive, etc.) by rotating the entire drillstring and where drilling fluid is utilized to rotate the bit of the drillstring. In such an example, a surface RPM (SRPM) may be determined by use of the surface equipment and a downhole RPM of the mud motor may be determined using various factors related to flow of drilling fluid, mud motor type, etc. As an example, in the combined rotating mode, bit RPM may be determined or estimated as a sum of the SRPM and the mud motor RPM, assuming the SRPM and the mud motor RPM are in the same direction.

As an example, a PDM mud motor may operate in a so-called sliding mode, when the drillstring is not rotated from the surface to drive a drill bit in a particular cutting direction. In such an example, a bit RPM may be determined or estimated based on the RPM of the mud motor. As an example, during a sliding mode, oscillation of a drillstring may be provided by surface equipment, for example, to oscillate the drillstring in a clockwise and a counter-clockwise direction, which may, for example, help to reduce risk of sticking, etc.

An RSS may drill directionally where there is continuous rotation from surface equipment, which may alleviate the sliding of a steerable motor (e.g., a PDM). An RSS may be deployed when drilling directionally (e.g., deviated, horizontal, or extended-reach wells). An RSS may aim to minimize interaction with a borehole wall, which may help to preserve borehole quality. An RSS may aim to exert a relatively consistent side force akin to stabilizers that rotate with the drillstring or orient the bit in the desired direction while continuously rotating at the same number of rotations per minute as the drillstring.

The LWD module 254 may be housed in a suitable type of drill collar and may contain one or a plurality of selected types of logging tools. It will also be understood that more than one LWD and/or MWD module may be employed. Where the position of a module is mentioned, as an example, it may refer to a module at the position of the LWD module 254, the MWD module 256, etc. An LWD module may include capabilities for measuring, processing, and storing information, as well as for communicating with the surface equipment. In the illustrated example, the LWD module 254 may include a seismic measuring device.

The MWD module 256 may be housed in a suitable type of drill collar and may contain one or more devices for measuring characteristics of the drillstring 225 and the drill bit 226. As an example, the MWD module 256 may include equipment for generating electrical power, for example, to power various components of the drillstring 225. As an example, the MWD module 256 may include the telemetry equipment 252, for example, where the turbine impeller may generate power by flow of the mud; it being understood that other power and/or battery systems may be employed for purposes of powering various components. As an example, the MWD module 256 may include one or more of the following types of measuring devices: a weight-on-bit measuring device, a torque measuring device, a vibration measuring device, a shock measuring device, a stick slip measuring device, a direction measuring device, and an inclination measuring device.

FIG. 2 also shows some examples of types of holes that may be drilled. For example, consider a slant hole 272, an S-shaped hole 274, a deep inclined hole 276 and a horizontal hole 278.

As an example, a drilling operation may include directional drilling where, for example, at least a portion of a well includes a curved axis. For example, consider a radius that defines curvature where an inclination with regard to the vertical may vary until reaching an angle between about 30 degrees and about 60 degrees or, for example, an angle to about 90 degrees or possibly greater than about 90 degrees.

As an example, a directional well may include several shapes where each of the shapes may aim to meet particular operational demands. As an example, a drilling process may be performed on the basis of information as and when it is relayed to a drilling engineer. As an example, inclination and/or direction may be modified based on information received during a drilling process.

As an example, deviation of a bore may be accomplished in part by use of one or more of an RSS, a downhole motor and/or a turbine. As to a motor, for example, a drillstring may include a positive displacement motor (PDM).

As an example, a system may be a steerable system and include equipment to perform a method such as geosteering. As an example, a steerable system may include a PDM or a turbine on a lower part of a drillstring which, just above a drill bit, a bent sub may be mounted. As an example, above a PDM, MWD equipment that provides real time or near real time data of interest (e.g., inclination, direction, pressure, temperature, real weight on the drill bit, torque stress, etc.) and/or LWD equipment may be installed. As to the latter, LWD equipment may make it possible to send to the surface various types of data of interest, including for example, geological data (e.g., gamma ray log, resistivity, density and sonic logs, etc.).

The coupling of sensors providing information on the course of a well trajectory, in real time or near real time, with, for example, one or more logs characterizing the formations from a geological viewpoint, may allow for implementing a geosteering method. Such a method may include navigating a subsurface environment, for example, to follow a desired route to reach a desired target or targets.

As an example, a drillstring may include an azimuthal density neutron (ADN) tool for measuring density and porosity; a MWD tool for measuring inclination, azimuth and shocks; a compensated dual resistivity (CDR) tool for measuring resistivity and gamma ray related phenomena; one or more variable gauge stabilizers; one or more bend joints; and a geosteering tool, which may include a motor and optionally equipment for measuring and/or responding to one or more of inclination, resistivity and gamma ray related phenomena.

As an example, geosteering may include intentional directional control of a wellbore based on results of downhole geological logging measurements in a manner that aims to keep a directional wellbore within a desired region, zone (e.g., a pay zone), etc. As an example, geosteering may include directing a wellbore to keep the wellbore in a particular section of a reservoir, for example, to minimize gas and/or water breakthrough and, for example, to maximize economic production from a well that includes the wellbore.

Referring again to FIG. 2, the wellsite system 200 may include one or more sensors 264 that are operatively coupled to the control and/or data acquisition system 262. As an example, a sensor or sensors may be at surface locations. As an example, a sensor or sensors may be at downhole locations. As an example, a sensor or sensors may be at one or more remote locations that are not within a distance of the order of about one hundred meters from the wellsite system 200. As an example, a sensor or sensor may be at an offset wellsite where the wellsite system 200 and the offset wellsite are in a common field (e.g., oil and/or gas field).

As an example, one or more of the sensors 264 may be provided for tracking pipe, tracking movement of at least a portion of a drillstring, etc.

As an example, the system 200 may include one or more sensors 266 that may sense and/or transmit signals to a fluid conduit such as a drilling fluid conduit (e.g., a drilling mud conduit). For example, in the system 200, the one or more sensors 266 may be operatively coupled to portions of the standpipe 208 through which mud flows. As an example, a downhole tool may generate pulses that may travel through the mud and be sensed by one or more of the one or more sensors 266. In such an example, the downhole tool may include associated circuitry such as, for example, encoding circuitry that may encode signals, for example, to reduce demands as to transmission. As an example, circuitry at the surface may include decoding circuitry to decode encoded information transmitted at least in part via mud-pulse telemetry. As an example, circuitry at the surface may include encoder circuitry and/or decoder circuitry and circuitry downhole may include encoder circuitry and/or decoder circuitry. As an example, the system 200 may include a transmitter that may generate signals that may be transmitted downhole via mud (e.g., drilling fluid) as a transmission medium.

As an example, one or more portions of a drillstring may become stuck. The term stuck may refer to one or more of varying degrees of inability to move or remove a drillstring from a bore. As an example, in a stuck condition, it might be possible to rotate pipe or lower it back into a bore or, for example, in a stuck condition, there may be an inability to move the drillstring axially in the bore, though some amount of rotation may be possible. As an example, in a stuck condition, there may be an inability to move at least a portion of the drillstring axially and rotationally.

As to the term "stuck pipe", this term may refer to a portion of a drillstring that cannot be rotated or moved axially. As an example, a condition referred to as "differential sticking" may be a condition whereby the drillstring cannot be moved (e.g., rotated or reciprocated) along the axis of the bore. Differential sticking may occur when high-contact forces caused by low reservoir pressures, high wellbore pressures, or both, are exerted over a sufficiently large area of the drillstring. Differential sticking may have time and financial cost.

As an example, a sticking force may be a product of the differential pressure between the wellbore and the reservoir and the area that the differential pressure is acting upon. This means that a relatively low differential pressure (delta p) applied over a large working area may be just as effective in sticking pipe as may a high differential pressure applied over a small area.

As an example, a condition referred to as "mechanical sticking" may be a condition where limiting or prevention of motion of the drillstring by a mechanism other than differential pressure sticking occurs. Mechanical sticking may be caused, for example, by one or more of junk in the hole, wellbore geometry anomalies, cement, keyseats or a buildup of cuttings in the annulus.

Various types of data associated with field operations may be 1-D series data. For example, consider data as to one or more of a drilling system, downhole states, formation attributes, and surface mechanics being measured as single or multi-channel time series data.

Figure 3:
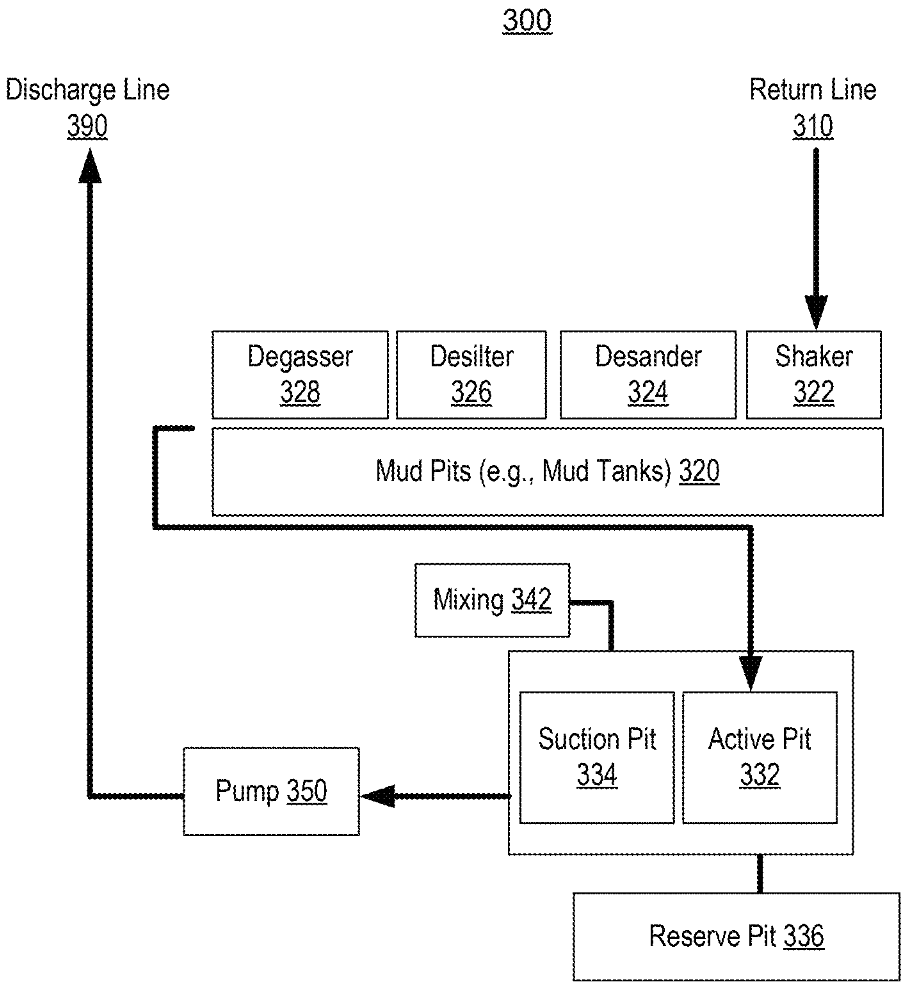
FIG. 3 illustrates an example of a system.

FIG. 3 shows an example of a drilling fluid system 300 that may aim to provide for various operations, which may include one or more of removing cuttings from a well, controlling formation pressures, suspending and releasing cutting, sealing permeable formations, maintaining wellbore stability, minimizing formation damage, cooling, lubricating and supporting a bit and drilling assembly, transmitting hydraulic energy to one or more downhole tools and/or a bit, ensuring adequate formation evaluation, controlling corrosion, facilitating cementing and completion, preventing gas hydrate formation, and minimizing impact on the environment.

As shown in the example of FIG. 3, the system 300 can include a return line 310 and a discharge line 390 (see also, e.g., the lines, pipes, hoses, etc., 206, 208, 209, 210, and 228 of FIG. 2). In the example of FIG. 3, the system 300 may include a shaker 322, a desander 324, a desilter 326, and a degasser 328 associated with various mud pits 320 (e.g., mud tanks) that can receive drilling fluid via the return line 310 and output processed drilling fluid to an active pit 332 that may be in fluid communication with a suction pit 334 and a reserve pit 336 where the suction pit 334 may be in fluid communication with a pump 350 that can pump drilling fluid to the discharge line 390. As an example, one or more mixing units 342 may be included, for example, for addition of one or more materials to the drilling fluid before it is pumped to the discharge line 390.

As an example, the system 300 may be utilized for one or more types of operations, which may include drilling, wireline, completions, blow out control, etc. As to completions, as an example, a cementing operation may include pumping and/or receiving of drilling fluid where cement may be positioned between casing and a borehole wall.

As an example, cuttings may be retrieved at surface, for example, using one or more of the components of the system 200 of FIG. 2, the system 300 of FIG. 3, etc. Cuttings can be produced as rock is broken by a drill bit advancing through a subsurface environment. As explained, cuttings may be carried to surface by drilling fluid (e.g., mud) circulating from one or more openings of a tool string such as, for example, openings of a drill bit of a drillstring. Drill cuttings may be separated from fluid using one or more types of equipment such as, for example, shale shakers, centrifuges, cyclone separators, etc. In cable-tool drilling, cuttings may be periodically bailed out of a bottom of a borehole. In auger drilling, cuttings may be carried to surface on auger flights.

As explained, during a drilling activity, a specific type of fluid can be injected from surface to bottom of a borehole through drill pipe where the fluid circulates back to surface as may be pushed by injection pressure (e.g., mud pumps, etc.). While scenarios may exist as to lost circulation, where a portion or all drilling fluid may be detrimentally lost to a formation (e.g., via fractures, faults, etc.), during normal drilling, some lesser amount of drilling fluid may be lost via filtration along with some suspended material, which may form a cake (e.g., a filter cake) along a borehole wall. Filter cake may be a residue deposited on a permeable medium when a slurry, such as a drilling fluid, is forced against the medium under a pressure. Filtrate may refer to liquid that passes through the medium, leaving the cake on the medium. Drilling fluids may be tested to determine filtration rate and filter-cake properties. Cake properties such as cake thickness, toughness, slickness and permeability can be relevant as the cake that forms on permeable zones in a borehole may cause stuck pipe and/or one or more other types of drilling problems. A certain degree of cake buildup may be desirable to isolate formations from drilling fluids. In openhole completions in high-angle or horizontal holes, formation of an external filter cake may be more beneficial than a cake that forms partly inside the formation, as the latter may have a higher potential for formation damage.

In contrast, lost circulation generally refers to reduced or total absence of fluid flow via an annulus when fluid is pumped through a tool string (e.g., drill pipe, etc.). Though the definitions of different operators may vary, reduction of flow may be classified as seepage (e.g., less than 20 bbl/hr or 3 $m^3$/hr), partial lost returns (e.g., greater than 20 bbl/hr or 3 $m^3$/hr but still some returns), and total lost returns (e.g., where no fluid comes out of the annulus). In this severe latter case, the hole may not remain full of fluid even if the pumps are turned off. If the hole does not remain full of fluid, the vertical height of the fluid column can be reduced and pressure exerted on an open formation(s) can be reduced. In turn, this may result in another zone flowing into a borehole, while the loss zone is taking mud, or even a catastrophic loss of well control. Even in the two less severe forms, the loss of fluid to the formation represents a detrimental loss of material with associated risks.

Figure 4:
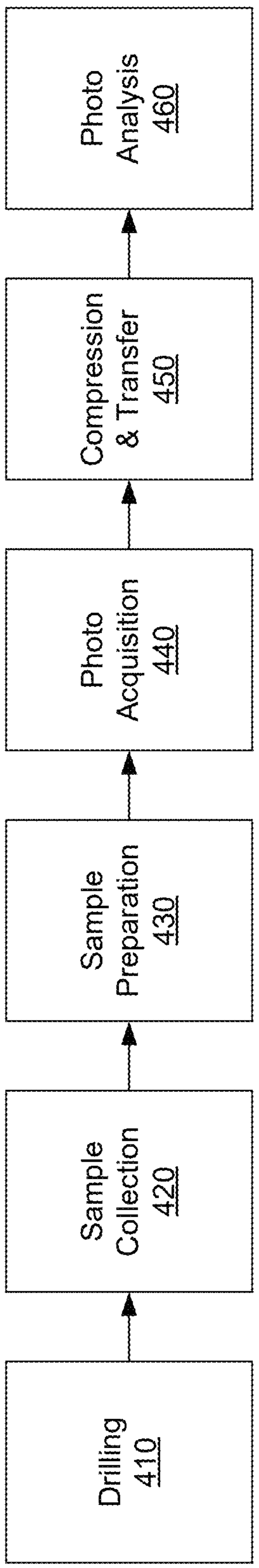
FIG. 4 illustrates an example of a workflow.

FIG. 4 shows an example of a workflow 400 pertaining to cuttings. In the example of FIG. 4, the workflow 400 includes various actions such as, for example, sample collection 410, sample preparation 420, photo acquisition 440, compression and transfer 450, and photo analysis 460. As explained, during normal operation, rocks crushed by a rotating drill bit may be transported to surface, for example, to a shale shaker. The cuttings may be separated by the shale shaker such that liquid and other components may be reused (e.g., circulated downhole). Cuttings, as rock particles, may be analyzed by mud loggers operating in a mud logging unit. Such analyses tend to be dependent on having one or more humans-in-the-loop (HITL). As an example, a system may provide for automation that may reduce demands on including one or more humans on site in a mud logging unit. For example, a system may provide for automating a workflow for cuttings analysis.

As an example, a workflow may include sample collection where cuttings (e.g., rock particles) are collected from a shaker and sample preparation where rock particles may be dried in an oven for analysis for example, or using other drying techniques. As an example, rock particles may be sieved using one or more meshes to select particles that fall in a certain range or ranges. In various instances, sieved rock particles may be specifically referred to as cuttings. As an example, sizes of one or more meshes may be from approximately 0.25 mm to approximately 3 mm for lower and upper bounds, respectively. As an example, cuttings (e.g., sieved particles) may be placed in a tray. In various instances, a tray may be prepared by a human where distribution of particles may be effectively random; for example, particles may be touching or piled in some areas in the tray and may be sparsely distributed in other areas. As to photography, a tray may be placed in front of a camera lens where photo acquisition may be performed with visible white light and with UV illumination (e.g., UV lamp, UV LEDs, etc.). As an example, to improve differentiation, a UV illuminated acquisition phase may include more than one captured image, for example, at one or more UV wavelengths (e.g., short UV light, long UV light, etc.) as may be known to produce fluorescence, which may relate to presence of hydrocarbons and/or presence of certain minerals. As an example, photography may be performed in the field at a field site where digital imagery, whether raw and/or processed, may be transmitted to one or more destinations that may be remote from the field site. As an example, digital imagery may be compressed using one or more compression techniques (e.g., lossless, lossy, etc.), which may facilitate transmission, particularly where transmission may be via a satellite network (e.g., consider remote locations, offshore rigs, etc.), which may have a low and/or costly bandwidth. As an example, a geologist may be present at a location, whether local and/or remote for purposes of analysis. As an example, analysis may aim to extract geologically meaningful information from cuttings imagery.

As an example, a system may be a multi-spectroscopy imaging system for rock characterization. For example, consider a dual-spectroscopy imaging system that includes at least one emission source in the ultraviolet (UV) spectrum. In such an example, another emission source may be in the visible spectrum. As an example, a system may be a dual-spectroscopy imaging system for rock characterization. As an example, a workflow may include performing one or more actions for calibration of a multi-spectroscopy imaging system for rock characterization.

As an example, a system may be an advanced imaging system that includes components for automating one or more aspects of a rock characterization workflow for applications such as environmental applications, industrial applications, etc. As an example, such a system may include multiple emissions sources for implementation of multi-spectroscopy techniques. For example, consider dual spectroscopy techniques that can include white-light direct absorption for color and texture analysis, and UV-induced fluorescence for hydrocarbon identification; noting that UV-induced fluorescence may also provide for characterization of one or more types of minerals.

As an example, so-called cut fluorescence may be performed. In such an example, a cut can refer to oil liberated from cuttings when a solvent is added. A common solvent used for inducing cuts may be chlorothene (e.g., 1,1,1-trichloroethane); noting that others may include acetone, petroleum ether, alcohol, hot water, and acid. Various solvents are flammable such that care is taken to handle materials safely. As an example, a cut may be performed while viewing rock samples under both normal and UV light. Solvent cuts may allow for deductions to be made regarding phenomena such as, for example, oil mobility and reservoir permeability. As an example, a cut may be described in terms of its natural color, fluorescence color, "liberation" rate and intensity, and residue. Suspected hydrocarbon-bearing intervals may be analyzed for cut fluorescence; noting that in various instances, there may be a positive cut fluorescence test when other hydrocarbon detection methods fail.

As an example, fluorescence scanning may provide for non-destructive, qualitative and quantitative results, which may be from cuttings and/or cores. As an example, steady-state fluorescence spectroscopy may be utilized to determine polycyclic aromatic hydrocarbon (PAH) content of oil and/or other hydrocarbon content. As to PAH content, due to the relatively high boiling points of PAHs, they tend to reside in rock for years, such that air exposure under standard conditions may not have a substantial impact on the ability to detect presence of PAHs.

As explained, hydrocarbons can fluoresce upon exposure to UV radiation. Various types of hydrocarbons emit light at longer wavelengths than the excitation light on their own or in organic solvents, due to aromatic hydrocarbons (AHs) that have aromatic structures and bear conjugated double bonds with intrinsic fluorescence properties in the ultraviolet-visible (UV-vis) region. Furthermore, AHs tend to be prominent fluorescent components in petroleum and may, depending on circumstances, predominate in fluorescence spectra. Hydrocarbon fluids that include different AH groups can exhibit different fluorescence characteristics.

As an example, a multi-spectroscopy system may be applied to analysis of cuttings and/or one or more other types of samples. For example, consider core analysis, water-hydrocarbon fluid analysis, drilling fluid analysis, etc.

As an example, to meet the requirements of multi-spectroscopy applications, a system may be an integrated optical system that achieves a wide field of view and ultra-high-resolution imaging. Such a system may be an optimized system that can enhance image sharpness and color accuracy for white-light imaging and that can provide high contrast over a relatively short exposure time for ultraviolet fluorescence imaging.

As an example, a system may provide for high-resolution imaging, UV fluorescence, machine vision, rock description generation, oil show identification for cuttings (e.g., drill cuttings).

As explained, a mud logger may perform mudlogging, which involves collection of fragments of drilled rock, known as cuttings, during drilling operations, which may then be prepared (e.g., rinsed and dried), and examined under a binocular microscope. Such meticulous examination includes a mud logger describing characteristics such as lithology, texture, color, grain size, and other pertinent physical characteristics. However, even under a microscope, identifying the presence of hydrocarbons within pores of cuttings can pose substantial challenges.

As explained, hydrocarbons may fluoresce responsive to illumination by UV radiation. As an example, a system may provide for improved mudlogging via exposing cuttings to UV radiation and capturing imagery that can include indicia of fluorescence. As an example, a system may provide for examining cuttings (e.g., a sample or cuttings sample) under UV light and evaluating fluorescence, for example, in terms of one or more of color, intensity, and distribution. As explained, a system may provide for automation that may reduce demands for a mud logger having to utilize a conventional fluoroscope and to visually assess such characteristics. However, the human eye may be limited and may not consistently characterize fluorescence. For example, a human or humans may inconsistently characterize color of fluorescence for one or more reasons. As an example, a system may provide for relatively consistent assessment of color of fluorescence, which may be in a manner that provides for increased automation and reduced reliance on subjective human visual observations and descriptions.

As an example, color of fluorescence can offer qualitative information about type of oil (e.g., hydrocarbon composition, etc.). As an example, a system may provide for application of an advanced UV spectroscopy technique known as quantitative fluorescence technology (QFT), which enables a quantitative assessment of oil measurements.

QFT provides for measurement of the fluorescence of crude oil extracted from a formation sample where intensity of the fluorescence is proportional to the amount of oil in the sample. An enhanced technique, referred to as QFT2, may provide for improved estimates of oil quantity and character from measurements made on drill cuttings or core samples. Such a technique may employ a two-point fluorescence measurement that yields estimates of both quantity (Weight % Oil) and oil type (API gravity). As an example, results may be combined with wire-line hydrocarbon porosity data to estimate volume percent oil in a formation, and resultant data may be further evaluated to estimate oil mobility.

While various petrophysical analyses and well testing workflows are performed to definitively establish commercially relevant oil quantities, mud loggers retain the responsibility of reporting and logging indications of hydrocarbons at an early stage during drilling. As an example, a system may provide for advanced UV fluorescence techniques that can be implemented at a wellsite, for example, as part of a dual spectroscopy imaging workflow. Such an approach may leverage advanced imaging techniques, combining white-light direct absorption for color and texture analysis with UV-induced fluorescence for hydrocarbon identification. The integration of such imaging technologies can aim to overcome various challenges that face mud loggers today. As an example, a system may offer a comprehensive and automated solution to enhance consistency and efficiency in rock characterization during drilling operations.

As explained, a multi-spectroscopy system may be a dual-spectroscopy system for imaging samples for one or more types of geological applications. Such an integrated system, for both white and UV imaging, can reduce demands for separate setups and help to ensure a seamless transition between imaging processes. As an example, a simultaneous collection of data from both imaging techniques may be performed to produce a comprehensive dataset, ultimately improving precision and uniformity of rock characterization.

As an example, a system may employ white-light imaging for rock color and texture analysis. Sedimentary rocks tend to be the most commonly seen rock types in an oil field and tend to be largely categorized based on their texture. As an example, a system can integrate a machine learning driven texture identification framework that provides for enhancing reliability of a drill cuttings description process at a wellsite. Implementation of such a system, on a relatively large scale, demands the capability to acquire a sufficient high-resolution, consistent, and information-rich image dataset. Such a dataset may be referred to as a training dataset, which may, for example, be utilized for training and/or testing and/or tuning (e.g., hyperparameter tuning) of one or more machine learning (ML) models.

As an example, a system may include integrated components and features that prioritize simplicity, cost-effectiveness, and consistent image quality for rock texture analysis. For example, consider a system that can streamline a workflow, with relatively rapid setup and calibration, rapid image acquisition, and real-time high-quality image transmission. Such a system may aim to achieve relatively high resolution and sharp focus for rock cuttings, for example, consider cuttings in a range of sizes from approximately 25 microns to approximately 3 mm. As an example, one or more processes may be performed using one or more types and/or sizes of meshes to extract cuttings of desired size or sizes from drilling fluid. As an example, a system may be transportable and robust to withstand wellsite deployment while remaining resilient to vibrations and/or other wellsite conditions.

As an example, a system can include a digital microscope including a machine vision lens attached to a high-resolution machine vision camera, connected to a portable computing device for purposes of image calibration and acquisition.

Figure 5:
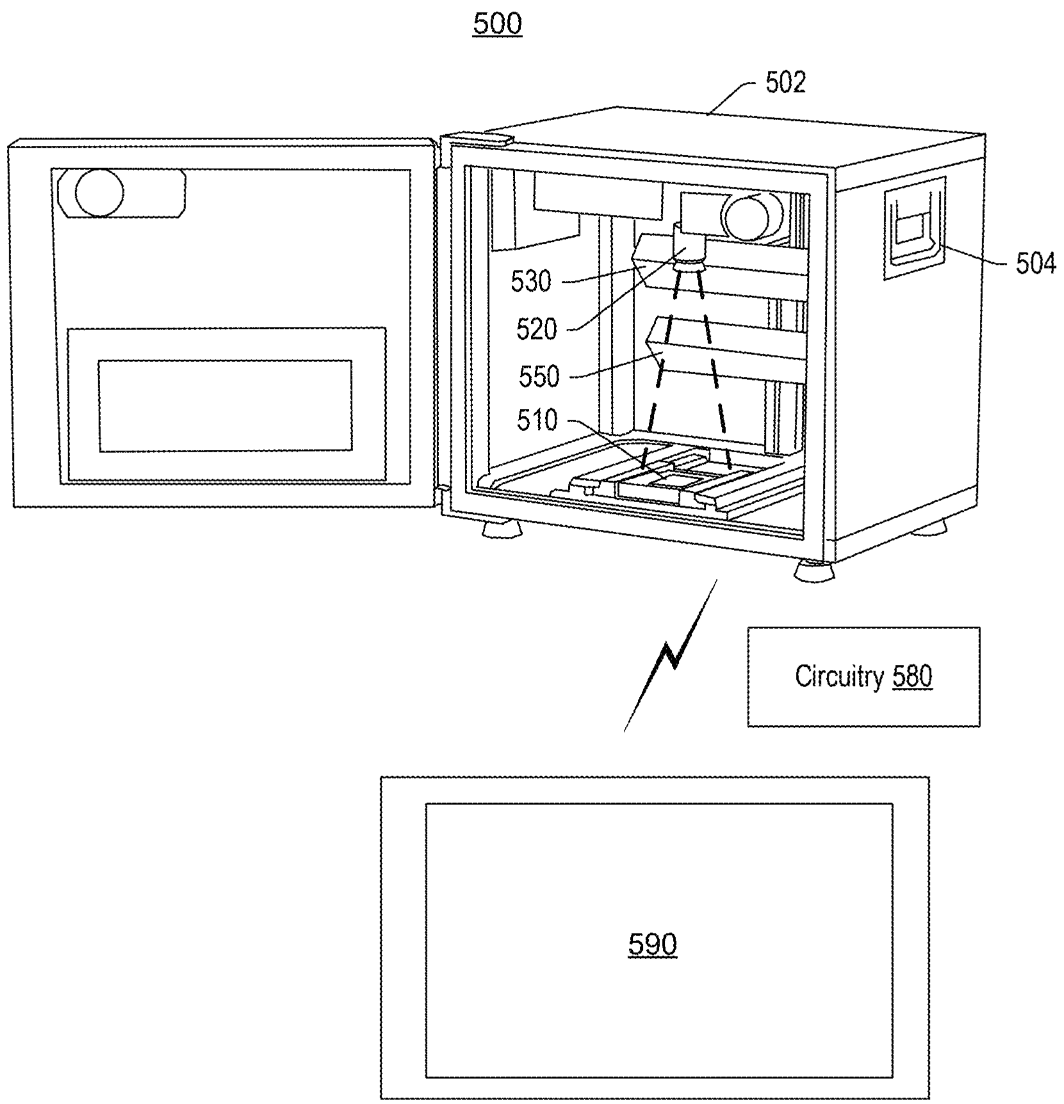
FIG. 5 illustrates an example of a system.

FIG. 5 shows an example of a system 500, as an approximate CAD rendering. As shown, the system 500 may include a case or housing 502, one or more handles 504, a cavity within the case or housing 502 that includes a sample holder 510, an imaging unit 520, and one or more illumination sources 530 and 550. The system 500 can include a digital microscope that is illuminated by an LED illuminator of 6500K temperature.

As shown in FIG. 5, the system 500 may include circuitry 580 that may include an interface or interfaces, one or more processors, memory, etc. The circuitry 580 may be embedded in a component or assembly within the case or housing 502 or operatively coupled thereto. As an example, a live-view image can be generated and rendered to a display 590 (e.g., consider a 21-inch display monitor to simplify sample inspection). The system 500 may be deployed at a wellsite to perform a cuttings description workflow at the wellsite. Such a system can include a high-resolution camera and multiple LED illuminations, for example, for white light and UV light (e.g., consider the illumination sources 530 as being for white light and the illumination sources 550 as being for UV light). Such a system may include handles, a lockable door, etc., which may facilitate transport by a human or humans (e.g., for loading in a vehicle, a cart, etc.). Such a system may include one or more interfaces for media, network, wire, fiber, etc., storage and/or transmission of digital data (e.g., digital image data). As an example, such a system may include one or more processors and associated memory that may store instructions that may be executable to perform one or more actions. As an example, such a system may include a controller, which may be processor-based.

As an example, the system 500 may include a white light source (see, e.g., the illumination source 530); an ultraviolet light source (see, e.g., the illumination source 550); a digital machine vision camera (see, e.g., the imaging unit 520) for capture of imagery of rock cutting samples illuminated by the white light source and the ultraviolet light source; and circuitry (see, e.g., the circuitry 580) operable to generate calibrated imagery of rock cuttings samples with contrast between rock cuttings samples with hydrocarbons and rock cuttings samples without hydrocarbons. In such an example, the imagery may be stored, processed, transmitted, displayed, etc. For example, consider rendering the imagery to the display 590, whether as raw, processed, compressed, decompressed, etc. As an example, processing may involve implementation of one or more machine learning models. In such an example, results may be output and utilized for controlling one or more operations, which may include one or more field operations, as may be associated with drilling (e.g., crushing rock with a drill bit).

As explained, a system may provide for UV fluorescence imaging for oil show identification. The presence of hydrocarbon inside cuttings pores, even under a microscope, may present challenges as to identification (e.g., presence or absence). In addressing this challenge, one or more UV fluorescence techniques may be employed, which may be within the context of drilling operations.

At a wellsite, a cuttings sample may be subjected to tests to screen for hydrocarbons. For example, a sample may be initially examined under UV light. In such an example, sample fluorescence can be evaluated in terms of color, intensity, and distribution, which, as mentioned, typically is a human-based process that relies on human visual observation by mud loggers using a conventional fluoroscope. While petrophysical analyses, coupled with well testing, may give a conclusive determination as to the presence of commercial quantities of oil, it remains a responsibility of a mud logger to report and log hydrocarbon shows.

Figure 6:
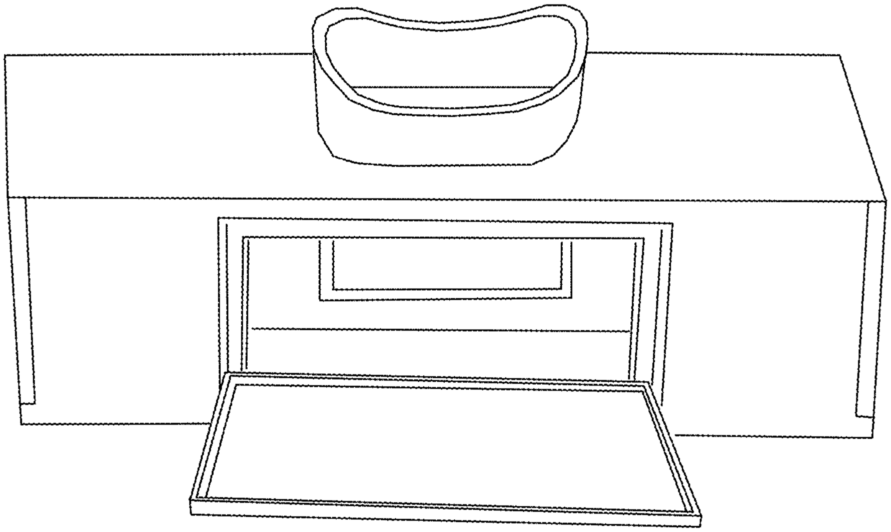
FIG. 6 illustrates an example of a human vision fluoroscope.
Figure 6:
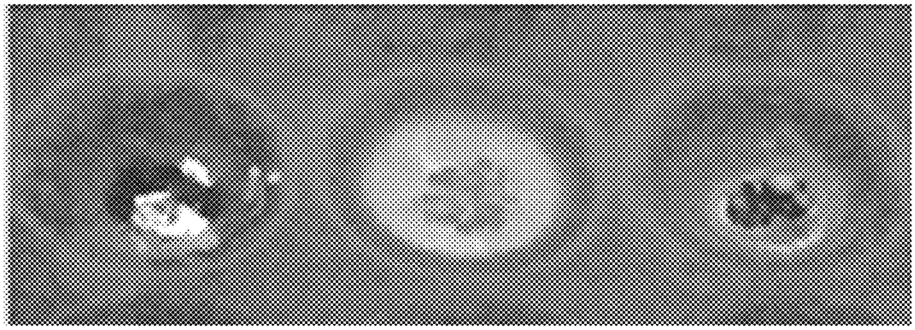

FIG. 6 shows an example of a human observation-based UV fluoroscope system 600 and an image 610 of what a human may see when a sample is subjected to UV radiation. In the image 610, fluorescence occurs under UV light as supplied by the fluoroscope system 600 where, in a leftmost portion of the image, mineral fluorescence may be frequently seen in rock samples. In the image 610, induced fluorescence can be observed in a center portion of the image, as may be created by immersing an oil-containing sample in a solvent. As an example, once the solvent evaporates, residual oil may produce a distinct fluorescence ring on a glass surface of the sample, as can be seen in a rightmost portion of the image 610.

In the fluorescence process, ultraviolet energy can be temporarily absorbed by a material and then emitted as lower-energy radiation, for example, in the visible light region. A legacy fluoroscope system as in FIG. 6, as commonly used in basic mudlogging, provides an eyepiece window to view the interaction of high-power UV radiation and drill cuttings. Such a human-operated and human observation-based fluoroscope tends to suffers from various issues. While an external camera may be added to such a fluoroscope, the fluoroscope itself provides for generally weak contrast images, which tend to be of limited utility. For example, such images may be poor candidates for use in a dataset for performing machine learning (e.g., training, testing, tuning, etc.). Various machine learning techniques can benefit from quality datasets, which may provide for better trained machine learning models, whether through training, testing, tuning, etc. Poor quality data can complicate generation of a trained machine learning model and may provide for less than acceptable output.

As explained, a system may include one or more machine learning models where, for example, such one or more machine learning models may be trained using relatively high-quality data (e.g., for training, testing and/or tuning). As an example, data may provide for reliably applying one or more machine learning tools for the detection of oil in drilled cuttings.

As to conventional UV fluoroscope systems, these may utilize one or more UV emitters that can pose one or more risks. For example, consider tube or bulb-based emitters that may demand a substantial amount of energy, include hazardous material and/or generate more than needed levels of radiation, which may, at times, be difficult to control (e.g., as to heat generation, amount of radiation and risks of radiation leakage, etc.). Conventional UV lamps typically use between 5 mg and 200 mg of mercury per lamp. Such UV lamps tend to demand routine replacement and while being susceptible to breakage during transportation, handling, and operation. Lamp-based emitters may be less robust to well-site conditions and, in general, less robust to handling by individuals that are often fit with personal protective equipment, which may make handling of such fragile lamp-based equipment challenging and fraught with risks. As explained, various lamps are mercury-based such that mercury may escape upon breakage, which may pose a risk in an enclosed or a non-enclosed environment.

As an example, a system may include digital imaging components that provide substantial advantages over visual inspection and documentation of oil fluorescence. As an example, a system may include a UV imaging subsystem that is designed to overcome various aspects of traditional fluoroscopes to offer a reliable solution for oil show identification in the field.

As an example, a system may be a system that has been subjected to component and component integration optimization. Addressing dual spectroscopy demands for achieving high-resolution white imaging and high-contrast UV fluorescence in high-resolution imaging involves a discerning selection of components, such as light sources, camera, and associated lens. Below, various aspects of a nuanced decision-making process underlying such selections are described, which aim to achieve a seamless integration that fulfills specific demands of each of visible light and UV imaging modalities.

As explained, UV light sources tend to be lamp-based (e.g., bulb or tube) that are reliant on ionized mercury emissions, with high-pressure mercury yielding a dominant peak at 365 nm (UVA region) and low-pressure mercury emitting predominantly at 254 nm (UVC region). For UV fluorescence applications, LED technology may be substituted, which may provide a more compact form, extended lifespan (e.g., up to 20000 hours), low power consumption, flexible operational modes (continuous or pulsed), improved thermodynamics, etc. As to thermal aspects, a lamp-based approach may emit heat energy that demands a substantial consideration of how much heat is transferred to a sample. For example, heat energy transferred to a sample may result in an increase in temperature that may be challenging to control. In contrast, UV LEDs may be more readily controlled, for example, using digital technology, where thermal concerns may be more readily addressed. As an example, UV LEDs may be regulated more rapidly than UV lamps, which may demand heat up and/or cool down times, which may stress glass of tubes or bulbs (e.g., increasing risks of breakage).

As to wavelengths of UV radiation, it may be considered to be defined within a wavelength range of approximately 10 nm to approximately 400 nm, which may be divided into bands, such as, for example: UVA (e.g., approx. 315 nm to approx. 400 nm); UVB (e.g., approx. 280 nm to approx. 315 nm); and UVC (e.g., approx. 100 to approx. 280 nm). In various instances, a near UV region, which lies closest to visible light, may be defined as including wavelengths between approx. 200 nm and approx. 400 nm, while a higher energy, shorter wavelength far UV region may be defined as spanning wavelengths between approx. 91 nm and approx. 200 nm. As to the visible band, it may be defined as ranging from wavelengths of approximately 380 nm to approximately 800 nm.

As explained, fluorescence spectrometry techniques find use in the petroleum industry. Some individual components of crude oil fluoresce within a well-defined range of wavelengths (e.g., approx. 275 nm to approx. 550 nm) when exposed to UV light; noting that emissions can be in the UV band and in the visible band.

Fluorescence spectrometry can involve fluorescence of aromatic hydrocarbons when illuminated by UV light where aromatic molecules absorb UV energy during radiation and immediately re-emit the light at a longer wavelength, where such re-emission is termed fluorescence. On a molecular level, fluorescence involves atoms and molecules changing energy levels when excited with high-energy UV light. Electrons in molecules can exist at a set of specific energy levels. As a result of what is termed Coulombic interaction between protons and orbiting electrons, the electrons may rest at their lowest energy orbital. When these electrons are excited with UV light they are promoted to a higher, less stable energy level. Once the electron is promoted it tends to fall back to its original more stable energy level and in doing so, gives off energy by emitting a photon. This electronic transition and emission from high-energy state to low energy state is called fluorescence emission.

As an example, differences may be noted between excitation and emission. For example, a difference between excitation (e.g., at 250 nm) and emission (e.g., at 275 nm to 550 nm) wavelengths may be referred to as Stokes shift. Specific hydrocarbon compounds may be identified by the magnitude of their Stokes shift. In general, as the number of aromatic rings increase, the fluorescent response may shift toward longer wavelengths. Hence, lighter compounds tend to fluoresce at shorter wavelengths while heavier compounds fluoresce at longer wavelengths. As to some examples of aromatic hydrocarbons, consider benzene, ethylbenzene, naphthalene, anthracene, chrysene, and benzo (a) pyrene; noting that various other hydrocarbons may fluoresce upon exposure to UV radiation.

Table 1, below, shows some examples of intensity of emissions from various materials, which include minerals (e.g., sand) and hydrocarbons. In various instances, fluoroscopy may be applied to detect presence of hydrocarbons as may be related to potential spills, leaks, etc. (e.g., spills on sand, spills in water, etc.). As explained, in a different context, fluoroscopy may be applied to cuttings, for example, to determine whether cuttings include hydrocarbons. In some instances, certain minerals in cuttings may fluoresce, a phenomenon that may cause a mineral to glow within the visible spectrum when exposed to UV; such minerals may be referred to as fluorescent minerals. Fluorescent minerals contain particles in their structure known as activators, which may respond to UV light by giving off a visible glow. In various instances, a system may provide for distinguishing mineral emissions from hydrocarbon emissions and/or otherwise accounting for mineral phenomena as may be related to exposure to UV light.

TABLE 1

Examples of Samples and Fluorescence Emissions

| Sample | Fl. Int. (V) 350 nm filter | Fl. Int. (V) 475+ nm filter |
|---|---|---|
| Clean Sand | 0.01 | 0.01 |
| Creosote (light) | <0.1 | 0.67 |
| Creosote (heavy) | <0.1 | 1.00 |
| Coal Tar (neat liquid) | <0.1 | 1.10 |
| Crude on Sand | 3.1 | 1.0 |
| Diesel on Sand | 3.1 | 0.55 |
| Gasoline on Sand | 6.3 | 0.83 |

As an example, a system can include one or more UV LEDs. In such an example, such one or more UV LEDs may be suitable for machine vision applications and be mated with or otherwise integrated with controller technology and, for example, waterproof protection. Such an approach can help to ensure stable illumination in a manner that may be relatively unaffected by external light interference, even during rapid processes. As an example, a system may employ functional accessories and advanced connection concepts to facilitate seamless integration of LED light sources into a digital imaging platform.

As illustrated in FIG. 5, an optical system design developed for lithology description may have a substantial working distance (e.g., larger than 100 mm), allowing for the incorporation of both white and UV light sources onto an optical stand. Considering demands for quasi-monochromatic UV light with minimal visible range emission for UV fluorescence, a system may integrate one or more filters such as, for example, an optical bandpass filter. As an example, an optical bandpass filter can have a transmission band surrounded by two blocking bands that allow only a portion of the spectrum to pass. To absorb visible light output, UV lights used for machine vision may integrate a UV filter that transmits a broad band of UVA with peak transmission at 365 nm.

Figure 7:
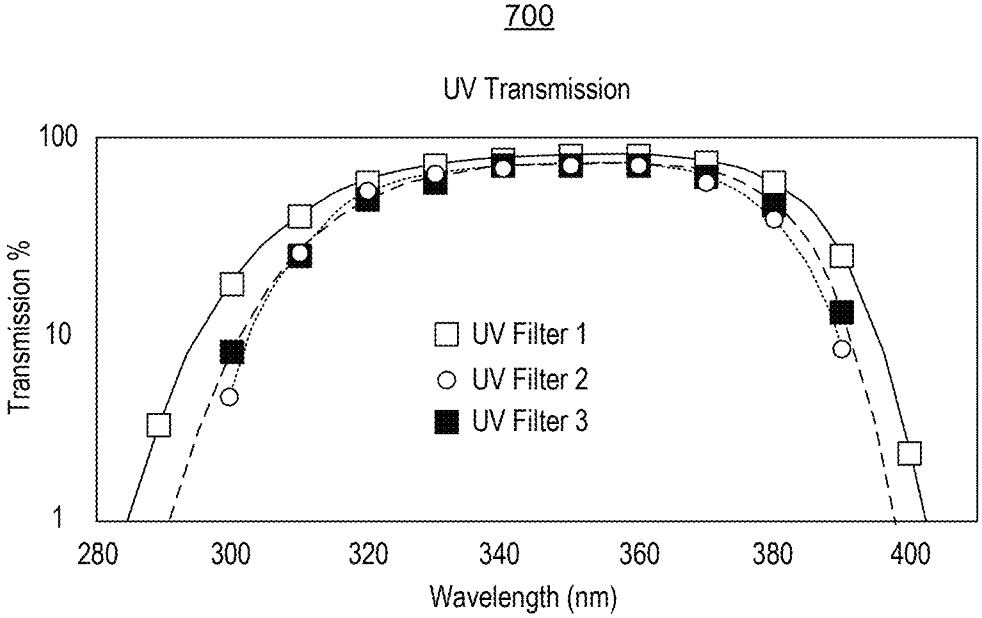
FIG. 7 illustrates an example of a plot.

FIG. 7 shows an example plot 700 that provides a comparison of the spectral selectivity of typical commercial UV filters. Specifically, the plot 700 provides a comparison of the transmission curve of three different commercial UV filters designed to improve the spectral purity of LED UV light emitted at 365 nm. High spectral selectivity may be often associated with a drop in the UV light intensity compared to unfiltered light. To address demands as to spectral purity and high intensity essential for UV fluorescence, a customized LED light design covering an entire imaging field of view (FOV) can be included in a system such as the system 500 of FIG. 5. Such an approach integrates high-performance LEDs with various optical systems, resulting in high-power irradiances precisely aligned with a target FOV.

As explained, a system can include a machine vision camera. Digital imaging offers substantial advantages over visual inspection using the naked eye when capturing UV-induced visible fluorescence. Exposure times of digital cameras (e.g., in the range of several seconds, etc.) tend to be influenced by the low intensity of the visible light being imaged. However, unlike limitations of human eyes, digital cameras afford precise control over exposure time. Digital cameras offer substantially enhanced control over color accuracy. As an example, a system may provide for selection of exposure time that is made carefully to amplify image brightness while concurrently minimizing color saturation, thereby preventing the loss of essential color information.

In comparison to high-resolution professional photography cameras (DSLRs), machine vision cameras, tend to be distinguished by their compact size and cost-effectiveness, which can offer advantages. Seamless integration into a system may be facilitated by ease of interfacing. Additionally, heightened reliability, as may be attributed to reduced number of or absence of moving parts, makes machine vision cameras particularly suitable for applications where robust operation is a plus. Flexibility of machine vision cameras can include compatibility with one or more optics standards, such as, for example, the C-mount, enhancing adaptability within various settings.

While modern CMOS sensors in digital cameras exhibit some inherent sensitivity to UVA, various cameras feature effective ultraviolet filtration over a sensor, which may be referred to as Bayer filters. In various instances, a Bayer filter may be grown/deposited directly onto a sensor. While Bayer filters are mentioned, as an example, one or more Foveon sensors may be employed, which may capture UV data (e.g., near UV, etc.) along with other data, including visible.

Various types of digital cameras may demand no additional filtration for satisfactory fluorescence photography. However, residual leakage or inadequate UV illumination may necessitate use of additional camera filtration in some cases to distinguish emitted fluorescent light.

Figure 8:
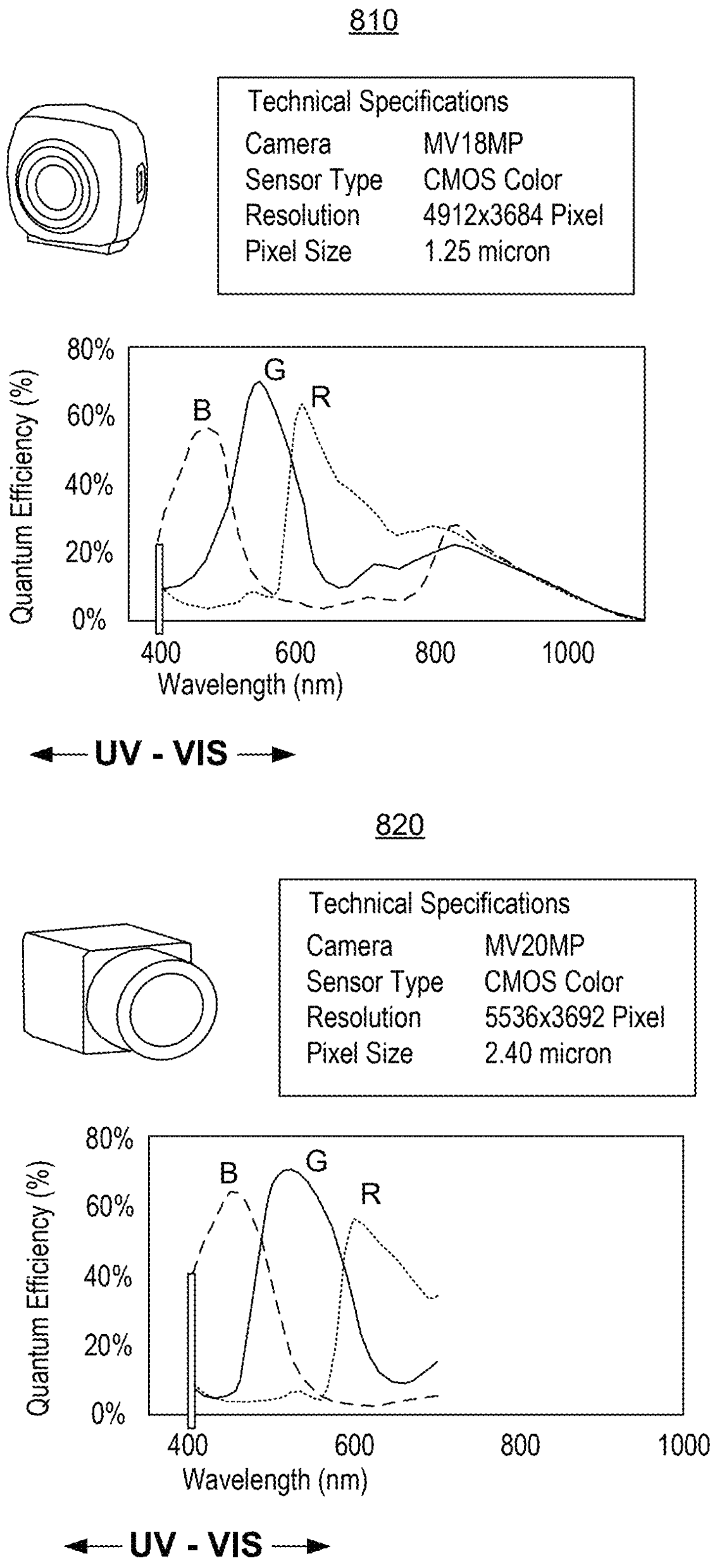
FIG. 8 illustrates examples of machine vision cameras.

FIG. 8 shows examples of digital machine vision cameras 810 and 820, along with spectral responses, labeled B for blue, G for green, and R for red. Specifically, the MV18MP camera 810 demonstrates superior UVA filtration efficiency compared to the MV20MP camera 820, as indicated by the camera sensor's lowest quantum efficiency value (i.e., the blue filter) at 400 nm. As shown, quantum efficiency is approximately 20 percent at approximately 400 nm for the camera 810 versus quantum efficiency of approximately 40 percent at approximately 400 nm for the camera 820. Hence, the camera 820 may be more susceptible to reflected UV light when compared to the camera 810.

As an example, a system may aim to facilitate seamless integration of UV fluorescence into a white light digital microscope. To achieve this, a system can include a machine vision camera that may provide for minimizing demand for additional filtration. Again, FIG. 8 shows spectral response of Bayer filters from two high-resolution cameras: MV18MP camera 810 and MV20MP camera 820 where the MV18MP camera 810 has a more efficient UVA filtration than the MV20MP camera 820, based on the quantum efficiency value at 400 nm Given selection of an appropriate machine vision camera, a suitable machine vision lens may be selected for inclusion in a dual-spectroscopy imaging system.

Figure 9:
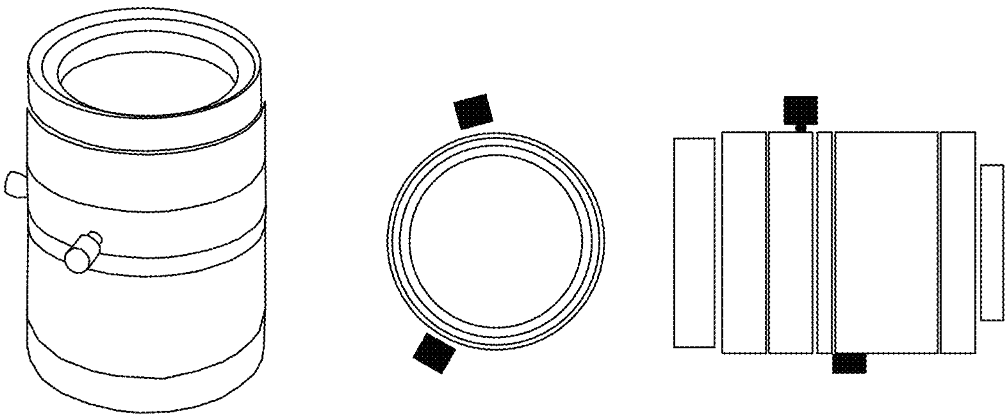
FIG. 9 illustrates an example of a lens and examples of light phenomena.
Figure 9:
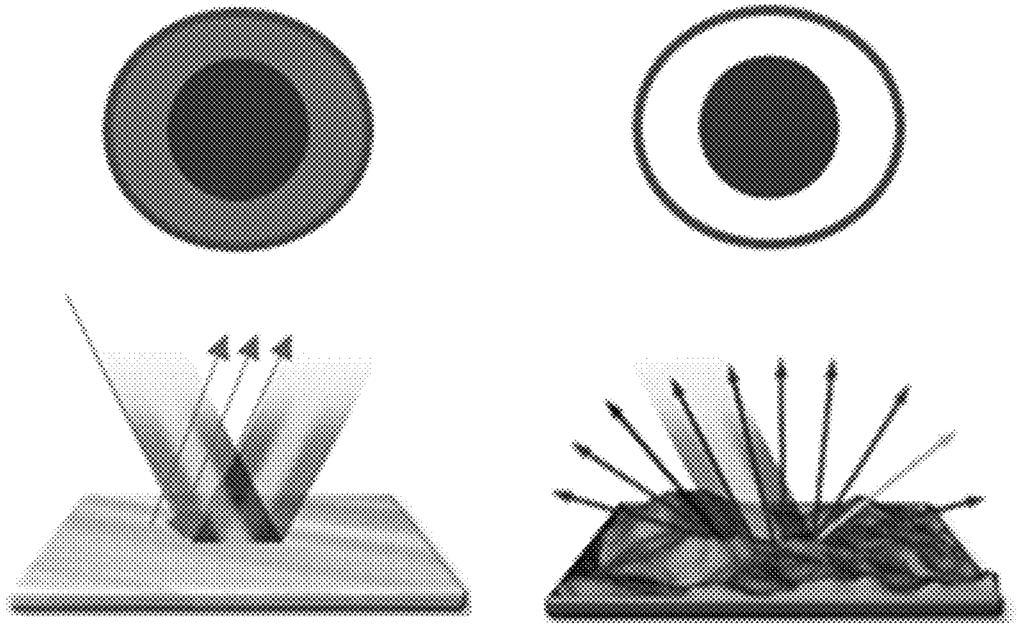

FIG. 9 shows an example of a machine vision lens 910 (e.g., perspective, end and side views) and examples of specular reflection of UV light and diffuse reflection of visible light. The lens 910 may be a CCTV type of lens, which may provide for control over lens iris and focus adjustment (e.g., manually and/or by machine). When conducting rock texture analysis, optimization of optical resolution demands attention. Such optimization can involve delicately balancing lens aberration and diffraction effects induced by the aperture. Accordingly, the lens numerical aperture may be configured at F/4 to meet criteria for white-light imaging. Such an approach can align with an overarching objective of maximizing system resolution to capture subtle variations in rock texture.

For UV fluorescence applications, a preference may be given to selecting a higher numerical aperture (e.g., F/8 or higher), for example, by closing the camera diaphragm to limit the impact of reflected UV light. The emitted visible fluorescence light can exhibit isotropic behavior and can be approximated by Lambert's emission law. As the reflected UV light is governed by specular reflection rules dependent on the relative orientation of the sample surface and the UV light, strategic adjustments can involve increasing the UV light orientation angle (e.g., beyond approximately 45° from the imaging axis) and/or concurrently reducing the lens aperture (e.g., F/8 or higher). Such an approach can effectively restrict the detection of reflected UV light while facilitating the collection of a sufficient portion of the emitted UV-induced visible light.

As to aperture, it is related to amount of light that can reach a sensor plane. In various instances, it may be desirable to collect as much light as possible, which may help to reduce exposure time, which may provide for increased throughput, reduced impact of vibrations, etc. However, a larger aperture stop may also require larger diameter optics, which may be heavier, more costly, etc. Aperture may also affect optical system properties. For example, opening size of an aperture stop is one factor that affects DOF (depth of field). A smaller stop (larger f number or F number) produces a longer (deeper) DOF because it only allows a smaller angle of a cone of light reaching an image plane (e.g., sensor plane) so the spread of the image of an object point is reduced. A longer (deeper) DOF allows objects at a wide range of distances from a viewpoint to all be in focus at the same time. In contrast, a larger stop (smaller f number or F number), has a shorter (shallower) DOF. An aperture stop may also limit the effect of optical aberrations by limiting light such that the light does not reach edges of optics where aberrations may be stronger than at optics centers. If the opening of the stop (e.g., the aperture) is too large, then an image may be distorted by stronger aberrations. In various instances, an optical system may include features (e.g., hardware and/or software) that may mitigate some effects of aberrations (e.g., allowing a larger aperture and therefore greater light collecting ability, if desired). The stop may also determine whether an image will be vignetted. Larger stops (smaller f number or F number) may cause the light intensity reaching the film or detector to fall off toward the edges of the image plane, especially when, for off-axis points, a different stop becomes the aperture stop by virtue of cutting off more light than did the stop that was the aperture stop on the optic axis. The stop location may also determine telecentricity. For example, if the aperture stop of a lens is located at the front focal plane of the lens, then it becomes image-space telecentricity, e.g., the lateral size of the image is insensitive to the image plane location; whereas, if the stop is at the back focal plane of the lens, then it becomes object-space telecentricity where the image size is insensitive to the object plane location. Telecentricity helps precise two-dimensional measurements because measurement systems with telecentricity tend to be more insensitive to axial position errors of samples or the sensor. In various instances, a lens may have one or more field stops, which may limit FOV. For example, when the FOV is limited by a field stop in the lens (e.g., rather than at a sensor), vignetting can result, which may present an issue if the resulting field of view is less than was desired.

As an example, one or more alternative approaches may include choosing a camera with low sensitivity to UV radiation, such as the MV18MP camera 810 while keeping the diaphragm open simultaneously to enhance optical resolution and diminish exposure time. Such an approach may allow for a unified hardware configuration catering to both white light and UV fluorescence applications, streamlining both hardware and software setups for convenient field deployment. As to depth of field (DOF), as explained, a sample may be presented on a tray where the size of individual pieces in the sample may be relatively small. For example, consider a scenario where the largest individual pieces may be of a size of approximately 3 mm (e.g., longest dimension). Hence, a DOF sufficient for such a size may be related to aperture selection and, for example, an ability to achieve acceptable focus. As explained, an aperture may be selected as to exposure time, which may be shortened where an aperture is selected to allow for more light to pass to a sensor of a digital machine vision camera.

As explained, a machine vision lens may be selected that includes aperture control. As explained, a comparison between UV light excitation controlled by specular reflection and visible fluorescence light emission controlled by diffuse reflection may facilitate selection of both incident light direction and lens aperture in a manner that allows for prioritizing fluorescence over UV light excitation, optionally alongside employing spectral filtration techniques.

Figure 10:
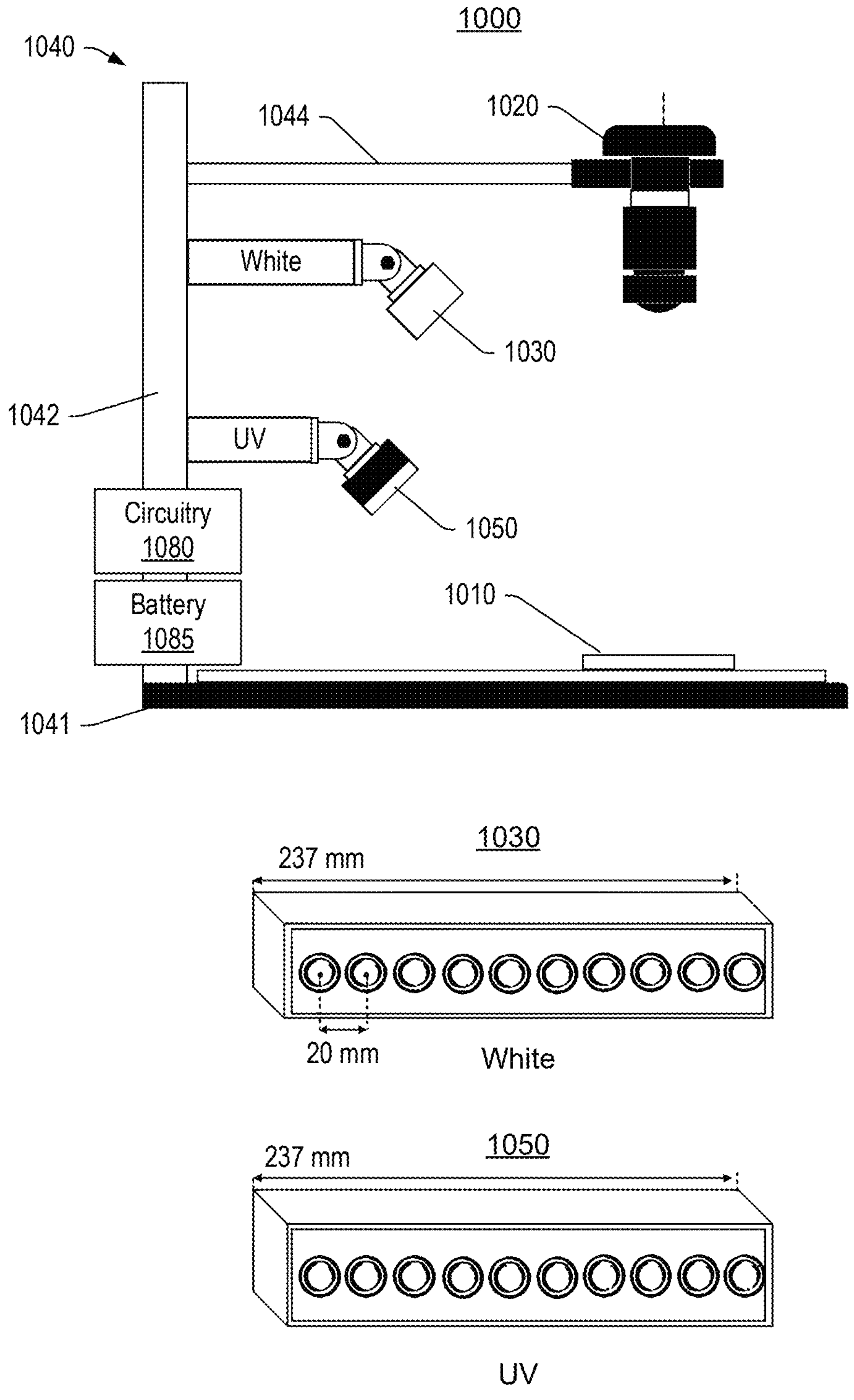
FIG. 10 illustrates an example of a system.

FIG. 10 shows an example system 1000 that includes selected components for white light and UV light, where the system 1000 was utilized to perform validation tests as to UV image quality. As shown, the system 1000 can include a sample tray or holder 1010, an imaging unit 1020, illumination sources for white light 1030, illumination sources for UV light 1050 and a stand or gantry 1040, which may include a base 1041, an upright 1042, and a cross-member 1044. In such an example, various components of the stand or gantry 1040 may be moveable or adjustable, which may be by hand and/or one or more motor, pneumatic, hydraulic, etc., mechanisms. As mentioned, a system may include a controller, which may provide for control of one or more components, which may be for operational and/or spatial control.

As shown in the example of FIG. 10, the system 1000 may include circuitry, which may include one or more processors, memory, etc. As an example, the system 1000 may include a battery 1085 as a power source. For example, consider one or more types of chemical batteries (e.g., lead (Pb), lithium-ion, etc.). As an example, an interface of the system 1000 may provide for receipt of power, such as, for example, electrical power. As an example, a system may include solar cells such that it may be supplied with power from the sun. As an example, a system may include solar cells within a chamber (e.g., a cavity), which may be able to recapture energy as may be emitted by one or more illumination sources.

As explained, suitable UV image quality can enhance application of one or more machine learning techniques or technologies. As an example, a system may include one or more computational frameworks for execution of instructions, which may pertain to machine learning, implementation of a trained machine learning model, etc. As an example, one or more models may provide for image classification and/or image segmentation and/or one or more other functions. As an example, one or more models may provide for handling of images captured using one or more types of illumination.

As explained, the system 1000 may include various components integrated therein, such as, for example, a number of white LEDs and a number of UV LEDs. The system 1000 may utilize a UV LED light source with a peak wavelength centered at 365 nm and a colored glass bandpass filter centered at the same wavelength. As explained, UV radiation (excitation) interacts with cuttings and excites electrons of fluorophores in crude oil, leading to emission mainly in the visible region of the electromagnetic spectrum. The fluorescence spectra of crude oil typically consist of a broad band in the visible region. The broadband arises from the overlapping emissions from the different fluorophores present in the sample. The system 1000 may use a CMOS image sensor to capture the visible photons from the sample fluorescence (emission).

As explained, a system may include a white-light digital microscope with a customized UV bar light with a UV filter. Within the UV LED light source, a selected UV bandpass filter can block visible photons from the tail end spectrum and thus reduces potential overlap between reflected visible light and UV-induced fluorescence light with the captured fluorescence images.

As an example, a system may provide for reducing impact of ambient light, for example, by performing measurements in a dark box (e.g., covering equipment using an opaque optical enclosure, etc.).

Figure 11:
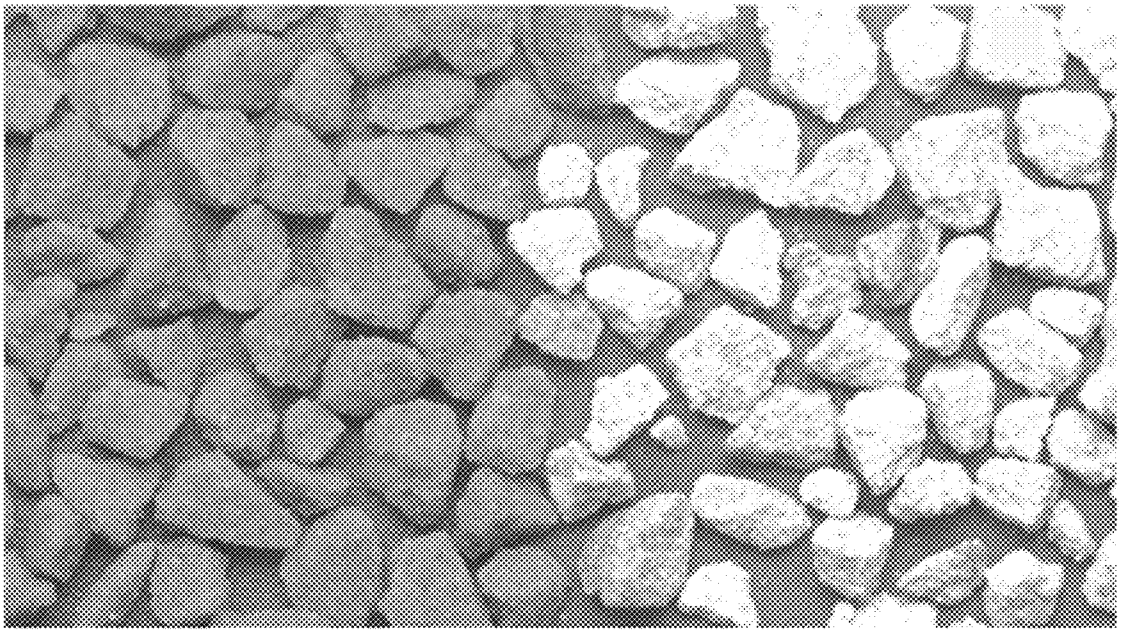
FIG. 11 illustrates examples of imagery.
Figure 11:
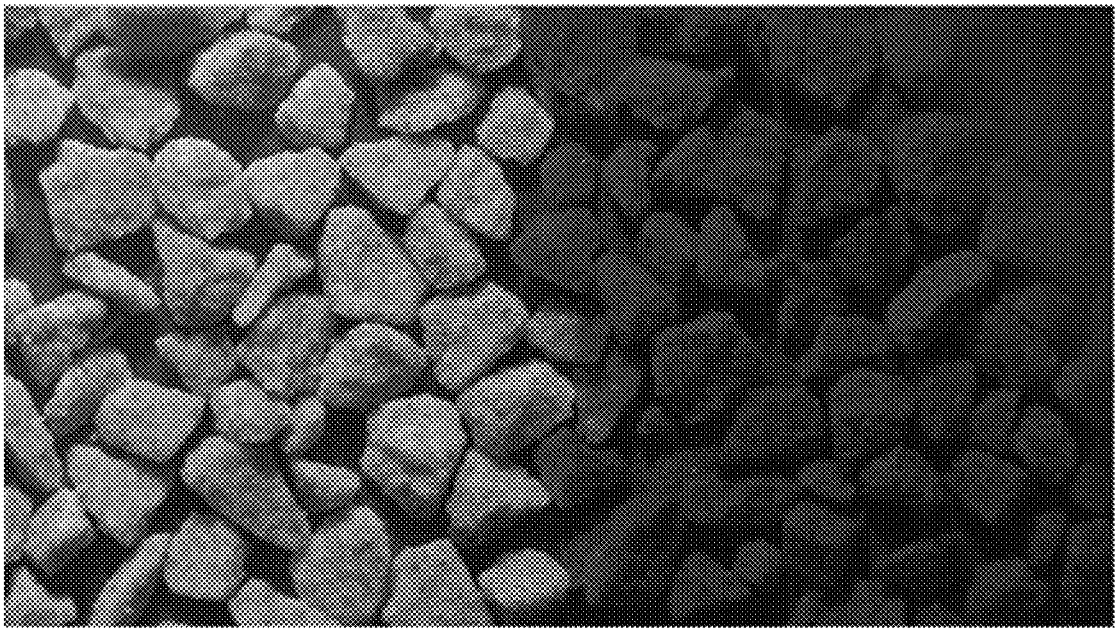

FIG. 11 shows example imagery 1110 and 1120 of white and UV light images of a mixture of dry (no oil) and oil-bearing cuttings using a machine vision camera. Specifically, the images are of a sandstone rock mixture under white light and UV light, where the left side of each image depicts the oil-bearing condition (e.g., oiled) while the right side illustrates the dry state, devoid of oil (e.g., unoiled).

In the imagery 1110 and 1120, cuttings mixtures of different colors were used to test the cuttings sample variability on the UV fluorescence system. The UV image of pixels with dry cuttings appear dark as imaged by the system, and the rock cuttings are not visible. In contrast, the pixels with oil-bearing cuttings are bright and luminescent. Longer exposure times or higher UV power only saturate the detector and do not impact the contrast between the cuttings with and without oil. High contrast improves an ability to rapidly identify oil-bearing cuttings and ensures a better image quality compared to that of a conventional fluoroscope fitted with a camera as may be used in a mud logger workflow.

As shown, a sufficient level of contrast can be obtained, which may provide for improved machine learning. As an example, contrast may also provide for assessment of intensity where, for example, level of intensity may be utilized to determine one or more characteristics (e.g., concentration of hydrocarbons, type of hydrocarbons, etc.). Accordingly, a system such as the system 500 of FIG. 5 may provide for generation of data suitable for training one or more types of machine learning models.

As an example, a system may provide for UV image calibration, for example, as to white balance and brightness control. There is currently no standard white balance method nor practical objective procedure for precise color accuracy in UV-induced fluorescence imaging. The standard white balance settings recommended by a camera manufacturer for white-light imaging calibration tend to be an initial recommendation. A final determination of color may be performed by comparing an image as displayed on a profiled monitor with the actual appearance of the object while under ultraviolet irradiation. As an example, a system may provide a captured image that provides fluorescence with substantially enhanced clarity and color intensity that also surpasses what the human eye can perceive due to the observation of very low-intensity fluorescence emission.

As an example, a workflow may include a calibration procedure. For example, consider the following: (1) selecting a fine sandstone sample to limit the impact of an irregular sample shape; (2) saturating about half of the rock sample using light oil or diesel; (3) taking an image of the UV-illuminated sample with the maximum intensity; (4) selecting two homogeneous regions of interest in the oil-saturated and original sample; (5) computing the mean luminance value for each region; and (6) adjusting the camera exposure to reach a high luminance value ($L^*>20$) for the oil-saturated region.

As an example, once optimal settings are determined, they may be standardized for fluorescence imaging using identical settings for the ultraviolet source and camera. To avoid diesel evaporation and preserve the calibration sample for a longer time, a single standard plate may be created for use as a quality control item of the fluorescence imaging system at the wellsite. As an example, a system may be utilized with one or more quality control items (e.g., plates, etc.).

As explained, a system was applied to assess rocks with and without hydrocarbons. Various aspects were considered in selection of system components, for example, based on results of UV fluorescence images as imaged with various filters and cameras. The selection process provided insights into the performance of the UV fluorescence imaging subsystem, while facilitating selection of adequate optical components.

Figure 12:
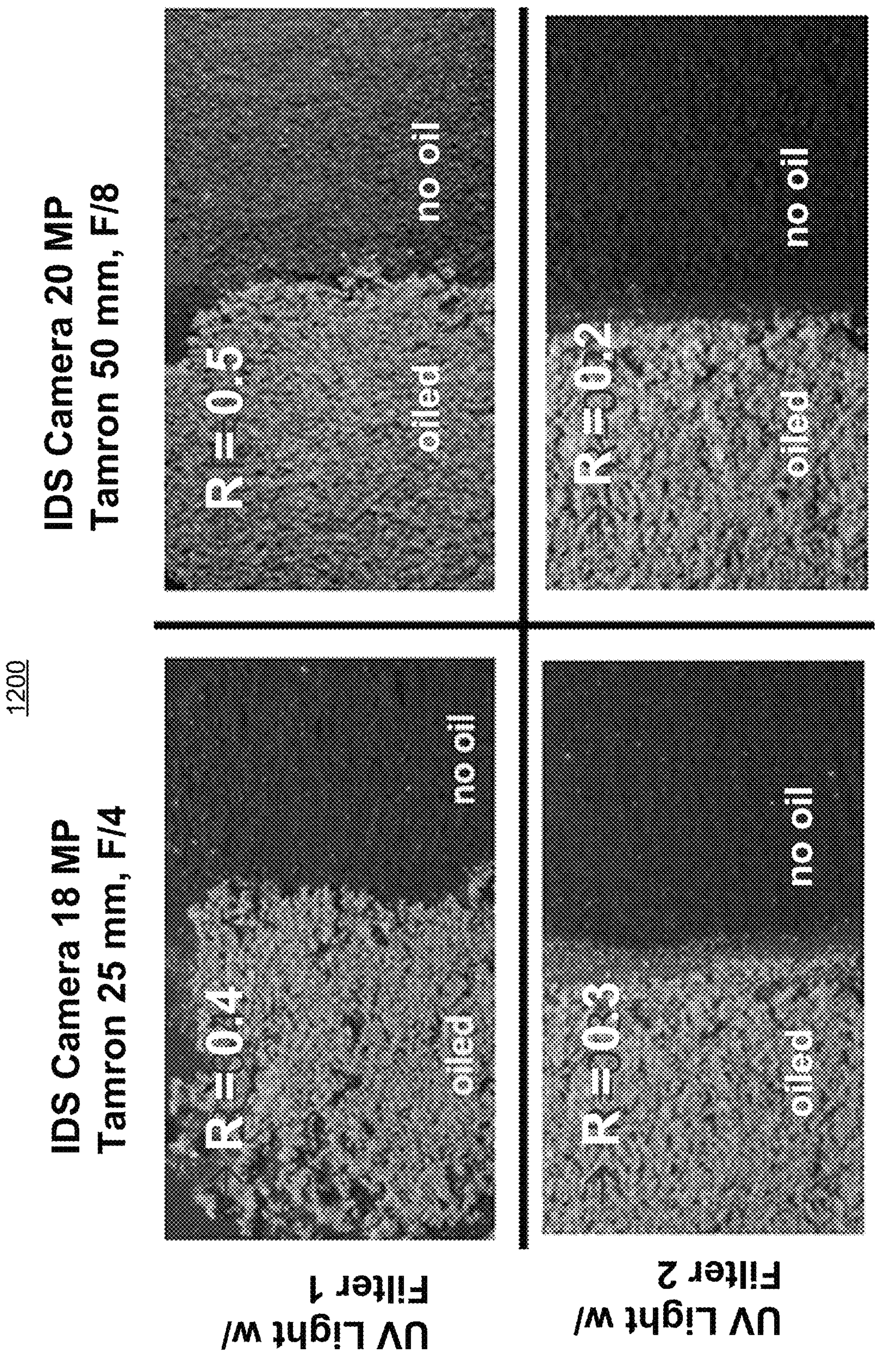
FIG. 12 illustrates examples of imagery.

FIG. 12 shows example results 1200, specifically, a comparison of UV fluorescence images acquired using UV LED lights with two different UV filters (filter #1 and filter #2) and two machine vision cameras (MV18MP and MV20MP). As an example, a method may include analyzing a fluorescence contrast parameter, denoted as the ratio (R), which may be derived from the luminance ($L^*$) values of the oiled and non-oiled regions of interest:

$$R = \frac{L^*_{dry-sample}}{L^*_{oiled-sample}}$$

As an example, low ratio values observed with tested filters suggest a superior fluorescence contrast achieved with a customized UV LED light (e.g., UV light with filter #2). This customized UV light provides a narrow bandpass selection around the central LED wavelength (365 nm) and minimizes the amount of emitted visible light (wavelength higher than 400 nm) from the excitation source that could otherwise degrade the UV excitation source.

Additionally, using the selected UV illumination equipped with filter #2, as shown in FIG. 12, allows for a comparison between two distinct machine vision cameras: MV18MP and MV20MP, each associated with the optimal lens configuration to enhance the UV fluorescence contrast ratio ($R<0.3$). However, despite comparable results in UV fluorescence imaging, the MV18MP camera demonstrated superior performance in white light imaging. The associated imaging system efficiently optimized image resolution and mitigated the impact of diffraction caused by the lens aperture (e.g., as may be aperture dependent). Moreover, the MV18MP camera outperforms the MV20MP camera in terms of UVA filtration capacity, making it a suitable choice for an efficient design of a dual spectroscopy system.

As explained, a system may be a multi-spectroscopy system suitable for obtaining imagery for white and UV illumination. Such a system may be a UV fluorescence system for mud logging, for example, to perform UV fluorescence spectroscopy as to samples that may or may not include hydrocarbons (e.g., crude oil, etc.). The differentiation in wavelength and direction between emission and excitation radiation allows such a fluorescence system to be effectively designed, effectively reducing detection of the UV incident beam (excitation) and thereby achieving heightened sensitivity to the fluorescent light (emission).

Through the adoption of digital imaging, substantial enhancements can be realized compared to the current oil show workflow, which relies on the human eye's detection of UV fluorescence. Notably, careful selection of the camera model, incorporating Bayer filters to block residual reflected UV light, and employing UV LED light equipped with an efficient UV bandpass filter to counteract any remaining emitted visible light, facilitates the optimization of fluorescence contrast.

As explained, an example system demonstrated that acceptable UV fluorescence contrast can be attained by utilizing machine vision UV light tailored to integrate a bandpass UV filter and combined with a machine vision camera with minimal sensitivity to UV light.

As an example, a dual spectroscopy imaging system that fulfills demands for both white-light and UV fluorescence imaging may also be suitable for field deployment (e.g., deployment at a wellsite) for application in a rock description workflow in the oil and gas industry.

Figure 13:
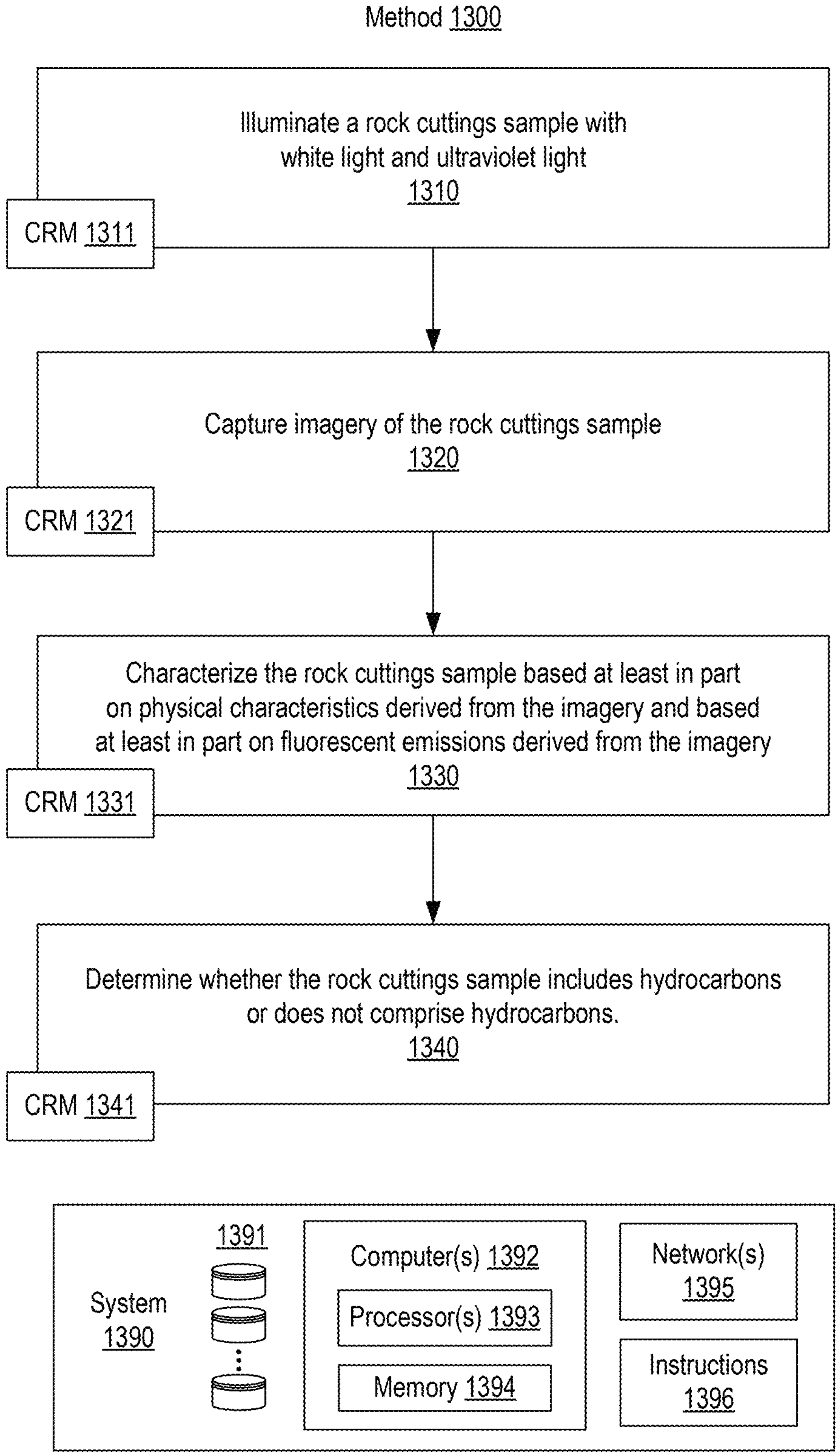
FIG. 13 illustrates an example of a method and an example of a system.

FIG. 13 shows an example of a method 1300 that includes an illumination block 1310 for illuminating a rock cuttings sample with white light and ultraviolet light; a capture block 1320 for capturing imagery of the rock cuttings sample; and a characterization block 1330 for characterizing the rock cuttings sample based at least in part on physical characteristics derived from the imagery and based at least in part on fluorescent emissions derived from the imagery. In such an example, the method 1300 may include a determination block 1340 for determining whether the rock cuttings sample includes hydrocarbons or does not include hydrocarbons.

FIG. 13 also shows various computer-readable media (CRM) blocks 1311, 1321, 1331, and 1341. Such blocks may include instructions that are executable by one or more processors, which may be one or more processors of a computational framework, a system, a computer, etc. A computer-readable medium may be a computer-readable storage medium that is not a signal, not a carrier wave and that is non-transitory. For example, a computer-readable medium may be a physical memory component that may store information in a digital format.

In the example of FIG. 13, a system 1390 includes one or more information storage devices 1391, one or more computers 1392, one or more networks 1395 and instructions 1396. As to the one or more computers 1392, each computer may include one or more processors (e.g., or processing cores) 1393 and a memory 1394 for storing the instructions 1396, for example, executable by at least one of the one or more processors. As an example, a computer may include one or more network interfaces (e.g., wired or wireless), one or more graphics cards, a display interface (e.g., wired or wireless), etc. The system 1390 may be specially configured to perform one or more portions of the method 1300 of FIG. 13.

As an example, a system may employ one or more machine learning models. For example, consider one or more trained machine learning models that may provide for receiving imagery of rock cuttings and outputting at least an indication of presence or absence of hydrocarbons. In such an example, one or more trained machine learning models may provide for outputting one or more characteristics of the rock cuttings, which may be physical characteristics. For example, consider one or more of rock type (e.g., with classification), color, texture (e.g., grain size, roundness, sorting), cement and/or matrix material, fossils, sedimentary structures, porosity, etc. As an example, oil show may be considered a characteristic based on fluorescence.

As an example, a system may be operated to capture imagery where a single image may provide for characterizations as to physical characteristics and hydrocarbons. As an example, a system may be operated using one or more techniques that may provide for digital control of a white light source and/or an ultraviolet light source. For example, consider pulsing where pulses may be controlled. In various instances, separate images may be acquired where one type of image may be without ultraviolet illumination and another type of image may be with ultraviolet illumination. As explained, a system may provide for simultaneous white light and ultraviolet illumination to generate a single image of a rock cuttings sample for purposes of determination of physical characteristics and presence of hydrocarbons, which may include determination as to what type of hydrocarbons and/or composition of hydrocarbons.

As an example, a system may provide for determinations as to one or more of contaminants, metal, drilling additives, lost-circulation material (LCM), suspected caved material, drilled-formation rock cuttings, etc. For example, consider a sample that may be prepared in one or more manners, which may be a raw sample and/or processed sample. As explained, a machine learning-based approach may be employed to make one or more types of determinations as to a sample as collected from drilling fluid (e.g., and/or as raw drilling fluid, etc.). As an example, output of a system may be in the form of one or more logs, which may include an estimate of percentage of each rock type, an interpretation of lithology, presence and/or type/composition of hydrocarbons, etc.

As explained, a system may provide for generation of training data, which may be utilized for one or more of training, testing, tuning, etc., one or more machine learning models. As explained, a system may provide for generation of imagery that can be suitably high in contrast between instances of no hydrocarbons in a sample and hydrocarbons in a sample. Such imagery may provide for robust training to allow for generation of a trained machine learning model that can improve automation, consistency, etc.

As an example, one or more image analysis machine learning models may be employed. As an example, a U-Net type of machine learning model may be employed. U-Net is an architecture that may be employed for various tasks (e.g., semantic segmentation, etc.). It can include a contracting path and an expansive path where the contracting path follows an architecture of a convolutional network. It may provide for repeated application of two 3×3 convolutions (unpadded convolutions), each followed by a rectified linear unit (ReLU) and a 2×2 max pooling operation with stride 2 for downsampling. In such an example, at each downsampling step it may be possible to double the number of feature channels. As an example, every step in an expansive path may provide for an upsampling of a feature map followed by a 2×2 convolution ("up-convolution") that halves the number of feature channels, a concatenation with the correspondingly cropped feature map from the contracting path, and two 3×3 convolutions, each followed by a ReLU. As an example, cropping may be employed due to loss of border pixels in each convolution. As an example, at a final layer, a 1×1 convolution may be used to map each 64-component feature vector to the desired number of classes. As an example, a total network may include 23 convolutional layers. As explained, one or more models may be utilized for one or more tasks, which may include, for example, one or more of classification and segmentation. As an example, a model may provide for feedback that can be utilized to instruct a system. For example, consider a model that may provide for generation of parameters for one or more settings of a system, which may include position, imaging, lighting, etc., types of settings.

As to types of machine learning models, consider one or more of a support vector machine (SVM) model, a k-nearest neighbors (KNN) model, an ensemble classifier model, a neural network (NN) model, etc. As an example, a machine learning model may be a deep learning model (e.g., deep Boltzmann machine, deep belief network, convolutional neural network, stacked auto-encoder, etc.), an ensemble model (e.g., random forest, gradient boosting machine, bootstrapped aggregation, AdaBoost, stacked generalization, gradient boosted regression tree, etc.), a neural network model (e.g., radial basis function network, perceptron, back-propagation, Hopfield network, etc.), a regularization model (e.g., ridge regression, least absolute shrinkage and selection operator, elastic net, least angle regression), a rule system model (e.g., cubist, one rule, zero rule, repeated incremental pruning to produce error reduction), a regression model (e.g., linear regression, ordinary least squares regression, stepwise regression, multivariate adaptive regression splines, locally estimated scatterplot smoothing, logistic regression, etc.), a Bayesian model (e.g., naïve Bayes, average on-dependence estimators, Bayesian belief network, Gaussian naïve Bayes, multinomial naïve Bayes, Bayesian network), a decision tree model (e.g., classification and regression tree, iterative dichotomiser 3, C4.5, C5.0, chi-squared automatic interaction detection, decision stump, conditional decision tree, M5), a dimensionality reduction model (e.g., principal component analysis, partial least squares regression, Sammon mapping, multidimensional scaling, projection pursuit, principal component regression, partial least squares discriminant analysis, mixture discriminant analysis, quadratic discriminant analysis, regularized discriminant analysis, flexible discriminant analysis, linear discriminant analysis, etc.), an instance model (e.g., k-nearest neighbor, learning vector quantization, self-organizing map, locally weighted learning, etc.), a clustering model (e.g., k-means, k-medians, expectation maximization, hierarchical clustering, etc.), etc.

As an example, a machine model, which may be a machine learning model (ML model), may be built using a computational framework with a library, a toolbox, etc., such as, for example, those of the MATLAB framework (MathWorks, Inc., Natick, Massachusetts). The MATLAB framework includes a toolbox that provides supervised and unsupervised machine learning algorithms, including support vector machines (SVMs), boosted and bagged decision trees, k-nearest neighbor (KNN), k-means, k-medoids, hierarchical clustering, Gaussian mixture models, and hidden Markov models. Another MATLAB framework toolbox is the Deep Learning Toolbox (DLT), which provides a framework for designing and implementing deep neural networks with algorithms, pretrained models, and apps. The DLT provides convolutional neural networks (ConvNets, CNNs) and long short-term memory (LSTM) networks to perform classification and regression on image, time-series, and text data. The DLT includes features to build network architectures such as generative adversarial networks (GANs) and Siamese networks using custom training loops, shared weights, and automatic differentiation. The DLT provides for model exchange various other frameworks.

As an example, the TENSORFLOW framework (Google LLC, Mountain View, CA) may be implemented, which is an open-source software library for dataflow programming that includes a symbolic math library, which may be implemented for machine learning applications that may include neural networks. As an example, the CAFFE framework may be implemented, which is a DL framework developed by Berkeley AI Research (BAIR) (University of California, Berkeley, California). As another example, consider the SCIKIT platform (e.g., scikit-learn), which utilizes the PYTHON programming language. As an example, a framework such as the APOLLO AI framework may be utilized (APOLLO.AI GmbH, Germany). As an example, a framework such as the PYTORCH framework may be utilized (Facebook AI Research Lab (FAIR), Facebook, Inc., Menlo Park, California).

As an example, a training method may include various actions that may operate on a dataset to train a ML model. As an example, a dataset may be split into training data and test data where test data may provide for evaluation. A method may include cross-validation of parameters and best parameters, which may be provided for model training.

The TENSORFLOW framework may run on multiple CPUs and GPUs (with optional CUDA (NVIDIA Corp., Santa Clara, California) and SYCL (The Khronos Group Inc., Beaverton, Oregon) extensions for general-purpose computing on graphics processing units (GPUs)). TENSORFLOW is available on 64-bit LINUX, MACOS (Apple Inc., Cupertino, California), WINDOWS (Microsoft Corp., Redmond, Washington), and mobile computing platforms including ANDROID (Google LLC, Mountain View, California) and IOS (Apple Inc.) operating system-based platforms.

TENSORFLOW computations may be expressed as stateful dataflow graphs; noting that the name TENSORFLOW derives from the operations that such neural networks perform on multidimensional data arrays. Such arrays may be referred to as "tensors".

As an example, a device may utilize TENSORFLOW LITE (TFL) or another type of lightweight framework. TFL is a set of tools that enables on-device machine learning where models may run on mobile, embedded, and IoT devices. TFL is optimized for on-device machine learning, by addressing latency (no round-trip to a server), privacy (no personal data leaves the device), connectivity (Internet connectivity is demanded), size (reduced model and binary size) and power consumption (e.g., efficient inference and a lack of network connections). TFL includes multiple platform support, covering ANDROID and iOS devices, embedded LINUX, and microcontrollers and diverse language support, which includes JAVA, SWIFT, Objective-C, C++, and PYTHON. TFL provides for high performance, with hardware acceleration and model optimization.

As an example, a system can include a white light source; an ultraviolet light source; a digital machine vision camera for capture of imagery of rock cutting samples illuminated by the white light source and the ultraviolet light source; and circuitry operable to generate calibrated imagery of rock cuttings samples with contrast between rock cuttings samples with hydrocarbons and rock cuttings samples without hydrocarbons. In such an example, the ultraviolet light sources can be or include ultraviolet LEDs.

As an example, an arrangement of sources and a digital machine vision camera may provide for reducing detection of an ultraviolet light incident beam of an ultraviolet light source to achieve heightened sensitivity to fluorescent light emission by hydrocarbons of a rock cutting sample with hydrocarbons. In such an example, the arrangement may include one or more Bayer filters to hinder capture of residual reflected ultraviolet light from the ultraviolet light incident beam by the digital machine vision camera.

As an example, a system may include one or more ultraviolet pass filters. For example, consider one or more ultraviolet pass filters that form an ultraviolet bandpass filter.

As an example, a system may include a trained machine learning model, for example, operable via circuitry to process imagery. As an example, such imagery may be calibrated imagery from a calibrated system, which may include one or more calibrated features (e.g., sources, filters, sensors, etc.).

As an example, circuitry may include a processor and memory accessible to the processor and an interface that receives digital data from a digital machine vision camera.

As an example, an ultraviolet light source of a system may have an orientation angle equal to or greater than 45 degrees with respect to an imaging axis of a digital machine vision camera.

As an example, a system may include a lens aperture size of a lens of a digital machine vision camera is less than or equal to F/4.

As an example, a digital machine vision camera may have a quantum efficiency at 400 nm that is less than 50 percent. In such an example, the quantum efficiency at 400 nm that is less than 50 percent may reduce impact of reflected ultraviolet light on imagery. As an example, a digital machine vision camera may have a quantum efficiency at 400 nm that is less than 40 percent. In such an example, the digital machine vision camera may include a lens that has a lens aperture of F/4.

As an example, a system may include circuitry that utilizes a fluorescence contrast parameter. In such an example, the fluorescence contrast parameter may be derived from luminance values of a rock cuttings sample with hydrocarbons and a rock cuttings sample without hydrocarbons. In such an example, the fluorescence contrast parameter may be a ratio of the luminance value of the rock cuttings sample without hydrocarbons to the luminance value of the rock cuttings sample with hydrocarbons.

As an example, a method can include illuminating a rock cuttings sample with white light and ultraviolet light; capturing imagery of the rock cuttings sample; and characterizing the rock cuttings sample based at least in part on physical characteristics derived from the imagery and based at least in part on fluorescent emissions derived from the imagery. In such an example, characterizing may include determining whether the rock cuttings sample includes hydrocarbons or does not include hydrocarbons.

As an example, one or more computer-readable storage media can include computer-executable instructions executable to instruct a computing system to: illuminate a rock cuttings sample with white light and ultraviolet light; capture imagery of the rock cuttings sample; and characterize the rock cuttings sample based at least in part on physical characteristics derived from the imagery and based at least in part on fluorescent emissions derived from the imagery.

As explained, a system may include one or more machine learning models, which may be resident locally and/or remotely. As example, a system may include a lightweight machine learning framework (e.g., TFL, etc.). As an example, a method may employ one or more machine learning models.

As an example, a method may be implemented in part using computer-readable media (CRM), for example, as a module, a block, etc. that include information such as instructions suitable for execution by one or more processors (or processor cores) to instruct a computing device or system to perform one or more actions. As an example, a single medium may be configured with instructions to allow for, at least in part, performance of various actions of a method. As an example, a computer-readable medium (CRM) may be a computer-readable storage medium (e.g., a non-transitory medium) that is not a carrier wave. As an example, a computer-program product may include instructions suitable for execution by one or more processors (or processor cores) where the instructions may be executed to implement at least a portion of a method or methods.

According to an embodiment, one or more computer-readable media may include computer-executable instructions to instruct a computing system to output information for controlling a process. For example, such instructions may provide for output to sensing process, an injection process, drilling process, an extraction process, an extrusion process, a pumping process, a heating process, etc.

Figure 14:
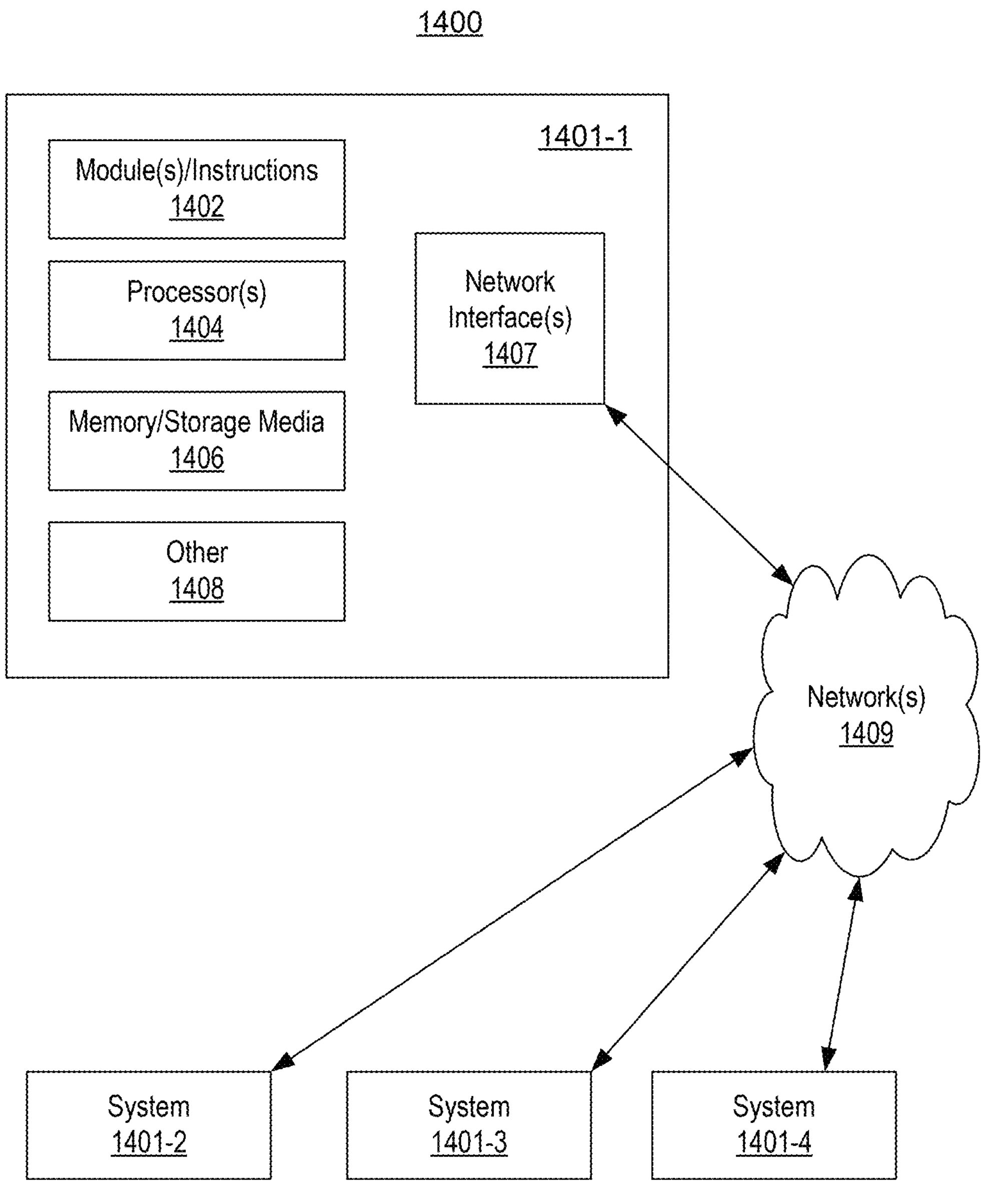
FIG. 14 illustrates an example of computing system.

In some embodiments, a method or methods may be executed by a computing system. FIG. 14 shows an example of a system 1400 that may include one or more computing systems 1401-1, 1401-2, 1401-3 and 1401-4, which may be operatively coupled via one or more networks 1409, which may include wired and/or wireless networks.

As an example, a system may include an individual computer system or an arrangement of distributed computer systems. In the example of FIG. 14, the computer system 1401-1 may include one or more modules 1402, which may be or include processor-executable instructions, for example, executable to perform various tasks (e.g., receiving information, requesting information, processing information, simulation, outputting information, etc.).

As an example, a module may be executed independently, or in coordination with, one or more processors 1404, which is (or are) operatively coupled to one or more storage media 1406 (e.g., via wire, wirelessly, etc.). As an example, one or more of the one or more processors 1404 may be operatively coupled to at least one of one or more network interface 1407. In such an example, the computer system 1401-1 may transmit and/or receive information, for example, via the one or more networks 1409 (e.g., consider one or more of the Internet, a private network, a cellular network, a satellite network, etc.). As shown, one or more other components 1408 may be included in the computer system 1401-1.

As an example, the computer system 1401-1 may receive from and/or transmit information to one or more other devices, which may be or include, for example, one or more of the computer systems 1401-2, etc. A device may be located in a physical location that differs from that of the computer system 1401-1. As an example, a location may be, for example, a processing facility location, a data center location (e.g., server farm, etc.), a rig location, a wellsite location, a downhole location, etc.

As an example, a processor may be or include a microprocessor, microcontroller, processor module or subsystem, programmable integrated circuit, programmable gate array, or another control or computing device.

As an example, the storage media 1406 may be implemented as one or more computer-readable or machine-readable storage media. As an example, storage may be distributed within and/or across multiple internal and/or external enclosures of a computing system and/or additional computing systems.

As an example, a storage medium or storage media may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLUERAY disks, or other types of optical storage, or other types of storage devices.

As an example, a storage medium or media may be located in a machine running machine-readable instructions, or located at a remote site from which machine-readable instructions may be downloaded over a network for execution.

As an example, various components of a system such as, for example, a computer system, may be implemented in hardware, software, or a combination of both hardware and software (e.g., including firmware), including one or more signal processing and/or application specific integrated circuits.

As an example, a system may include a processing apparatus that may be or include a general-purpose processors or application specific chips (e.g., or chipsets), such as ASICs, FPGAs, PLDs, or other appropriate devices, which may be or may include circuitry.

As an example, a device may be a mobile device that includes one or more network interfaces for communication of information. For example, a mobile device may include a wireless network interface (e.g., operable via IEEE 802.11, ETSI GSM, BLUETOOTH, satellite, etc.). As an example, a mobile device may include components such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

As an example, a system may be a distributed environment, for example, a so-called "cloud" environment where various devices, components, etc. interact for purposes of data storage, communications, computing, etc. As an example, a device or a system may include one or more components for communication of information via one or more of the Internet (e.g., where communication occurs via one or more Internet protocols), a cellular network, a satellite network, etc. As an example, a method may be implemented in a distributed environment (e.g., wholly or in part as a cloud-based service).

As an example, information may be input from a display (e.g., consider a touchscreen), output to a display or both. As an example, information may be output to a projector, a laser device, a printer, etc. such that the information may be viewed. As an example, information may be output stereographically or holographically. As to a printer, consider a 2D or a 3D printer. As an example, a 3D printer may include one or more substances that may be output to construct a 3D object. For example, data may be provided to a 3D printer to construct a 3D representation of a subterranean formation. As an example, layers may be constructed in 3D (e.g., horizons, etc.), geobodies constructed in 3D, etc. As an example, holes, fractures, etc., may be constructed in 3D (e.g., as positive structures, as negative structures, etc.).

Although only a few examples have been described in detail above, those skilled in the art will readily appreciate that many modifications are possible in the examples. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

BIBLIOGRAPHY (DOCUMENTS INCORPORATED BY REFERENCE HEREIN)

[1] Riecker, R. E., "Hydrocarbon fluorescence and migration of petroleum," *AAPG Bulletin* 46 (1), 60-75 (1962).

[2] Reyes, M. V., "Application of fluorescence techniques for mud-logging analysis of oil drilled with oil-based muds," *SPE Formation Evaluation* 9 (04), 300-305 (1994).

[3] Delaune, P. L., Spilker, K. K., Hanson, S. A., Wright, A. C., and Quagliaroli, R., "Enhanced Wellsite Technique for Oil Detection and Characterization," *SPE Annual Technical Conference and Exhibition*, SPE-56802-MS (1999).

[4] Di Santo, S., Yamada, T., Bondabou, K., and Ammar, M., "The digital revolution in mudlogging: An innovative workflow for advanced analysis and classification of drill cuttings using computer vision and machine-learning," in [*SEG International Exposition and Annual Meeting*], SEG (2022).

[5] Liu, K., Sherwood, N., and Zhao, M., "Advances in fluorescence spectroscopy for petroleum geosciences," (2014).

[6] Mullins, O. C., *The Physics of Reservoir Fluids: Discovery Through Downhole Fluid Analysis*, Schlumberger, Houston, TX (2008).

[7] Ablard, P., Bell, C., Cook, D., Fornasier, I., Poyet, J.-P., Sharma, S., Fielding, K., Lawton, L., Haines, G., Herkommer, M. A., et al., "The expanding role of mud logging," *Oilfield Review* 24 (1), 24-41 (2012).

What is claimed is:

1. A system comprising:

a white light source;

an ultraviolet light source;

a digital machine vision camera for capture of imagery of rock cutting samples illuminated by the white light source and the ultraviolet light source; and circuitry operable to generate calibrated imagery of rock cuttings samples with contrast between rock cuttings samples with hydrocarbons and rock cuttings samples without hydrocarbons.

2. The system of claim 1, wherein the ultraviolet light sources comprise ultraviolet LEDs.

3. The system of claim 1, wherein an arrangement of the sources and the digital machine vision camera reduce detection of an ultraviolet light incident beam of the ultraviolet light source to achieve heightened sensitivity to fluorescent light emission by hydrocarbons of a rock cutting sample with hydrocarbons.

4. The system of claim 3, wherein the arrangement comprises one or more Bayer filters to hinder capture of residual reflected ultraviolet light from the ultraviolet light incident beam by the digital machine vision camera.

5. The system of claim 1, comprising one or more ultraviolet pass filters.

6. The system of claim 5, wherein the one or more ultraviolet pass filters form an ultraviolet bandpass filter.

7. The system of claim 1, comprising a trained machine learning model operable via the circuitry to process the calibrated imagery.

8. The system of claim 1, wherein the circuitry comprises a processor and memory accessible to the processor and an interface that receives digital data from the digital machine vision camera.

9. The system of claim 1, wherein the ultraviolet light source comprises an orientation angle equal to or greater than 45 degrees with respect to an imaging axis of the digital machine vision camera.

10. The system of claim 1, wherein a lens aperture size of a lens of the digital machine vision camera is less than or equal to F/4.

11. The system of claim 1, wherein the digital machine vision camera comprises a quantum efficiency at 400 nm that is less than 50 percent.

12. The system of claim 11, wherein the quantum efficiency at 400 nm that is less than 50 percent reduces impact of reflected ultraviolet light on the imagery.

13. The system of claim 12, wherein the digital machine vision camera comprises a quantum efficiency at 400 nm that is less than 40 percent.

14. The system of claim 13, wherein the digital machine vision camera comprises a lens that comprises a lens aperture of F/4.

15. The system of claim 1, wherein the circuitry utilizes a fluorescence contrast parameter.

16. The system of claim 15, wherein the fluorescence contrast parameter is derived from luminance values of a rock cuttings sample with hydrocarbons and a rock cuttings sample without hydrocarbons.

17. The system of claim 16, wherein the fluorescence contrast parameter is a ratio of the luminance value of the rock cuttings sample without hydrocarbons to the luminance value of the rock cuttings sample with hydrocarbons.

18. A method comprising:

illuminating a rock cuttings sample with white light and ultraviolet light;

capturing imagery of the rock cuttings sample; and characterizing the rock cuttings sample based at least in part on physical characteristics derived from the imagery and based at least in part on fluorescent emissions derived from the imagery.

19. The method of claim 18, wherein the characterizing comprises determining whether the rock cuttings sample comprises hydrocarbons or does not comprise hydrocarbons.

20. Non-transitory one or more computer-readable storage media comprising computer-executable instructions executable to instruct a computing system to: illuminate a rock cuttings sample with white light and ultraviolet light; capture imagery of the rock cuttings sample; and characterize the rock cuttings sample based at least in part on physical characteristics derived from the imagery and based at least in part on fluorescent emissions derived from the imagery.

* * * * *